United States Patent [19]

Ishikawa et al.

[11] 4,317,820

[45] Mar. 2, 1982

[54] β-LACTAM SERIES COMPOUND AND ANTIBACTERIAL PHARMACEUTICAL COMPOSITION CONTAINING THE SAME

[75] Inventors: Hiroshi Ishikawa; Fujio Tabusa; Kazuyuki Nakagawa, all of Tokushima, Japan

[73] Assignee: Otsuka Pharmaceutical Co., Ltd., Tokyo, Japan

[21] Appl. No.: 28,770

[22] Filed: Apr. 10, 1979

[30] Foreign Application Priority Data

Apr. 12, 1978 [JP] Japan ................................. 53-43624
Sep. 7, 1978 [JP] Japan ................................ 53-110464
Nov. 16, 1978 [JP] Japan ................................ 53-141785
Nov. 24, 1978 [JP] Japan ................................ 53-145638

[51] Int. Cl.³ .................. A61K 31/545; C07D 499/70; C07D 501/32
[52] U.S. Cl. ................................ 424/246; 260/239.1; 424/256; 424/258; 424/263; 544/22; 544/25; 544/27; 544/28
[58] Field of Search .................... 260/239.1; 424/256, 424/258, 263, 246; 544/25, 27, 28, 22

[56] References Cited

U.S. PATENT DOCUMENTS

| | | | |
|---|---|---|---|
| 3,778,432 | 12/1973 | Pines | 260/239.1 |
| 3,780,034 | 12/1973 | Christensen et al. | 260/239.1 X |
| 3,954,731 | 5/1976 | Spitzer | 260/239.1 |
| 3,962,214 | 6/1976 | Goodson et al. | 260/239.1 |
| 3,975,375 | 8/1976 | Konig et al. | 260/239.1 |
| 4,062,842 | 12/1977 | Dolfini et al. | 260/239.1 X |

Primary Examiner—Natalie Trousof
Assistant Examiner—Vera C. Clarke
Attorney, Agent, or Firm—Sughrue, Mion, Zinn, Macpeak and Seas

[57] ABSTRACT

A β-lactam series compound represented by the formula (I):

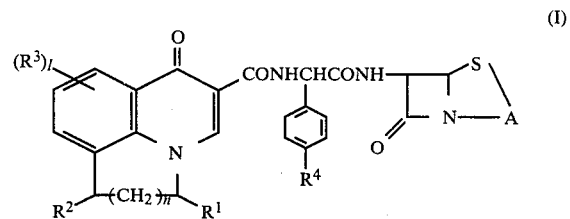

wherein $R^1$ represents a hydrogen atom or a lower alkyl group; $R^2$ represents a hydrogen atom; $R^3$ represents a halogen atom, a nitro group, an amino group, a hydroxy group, a lower alkyl group, a lower alkoxy group, a lower alkanoylamino group, a lower alkanesulfonyloxy group or a group represented by the formula

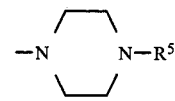

where $R^5$ represents a hydrogen atom, a lower alkanoyl group, or a lower alkanesulfonyl group; $R^4$ represents a hydrogen atom or a hydroxy group; n is 0 or 1; l is 0, 1 or 2; and A represents —C(CH₃)₂—CH(COOH)— or —CH₂C(CH₂R⁶)=C(COOH)— where $R^6$ represents a lower alkanoyloxy group, a group represented by the formula

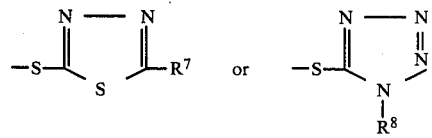

where $R^7$ and $R^8$ each represents a lower alkyl group and when n is 0, $R^1$ and $R^2$ can combine to form a cyclohexane ring together with the carbon atoms to which they are attached, and pharmaceutically acceptable salts thereof as well as a method for preparing same are disclosed. These compounds have antimicrobial activity.

32 Claims, No Drawings

β-LACTAM SERIES COMPOUND AND ANTIBACTERIAL PHARMACEUTICAL COMPOSITION CONTAINING THE SAME

BACKGROUND OF THE INVENTION

1. Field of the Invention

This invention relates to β-lactam derivatives represented by the formula (I) hereinafter defined and the pharmaceutically acceptable salts thereof which are useful as antimicrobial agents, a process for preparing the same and a pharmaceutical composition containing β-lactam derivatives.

2. Description of the Prior Art

It is known that certain types of polyheterocyclic compounds exhibit antimicrobial activity. For example, U.S. Pat. No. 3,917,609 to Gerster et al discloses substituted derivatives of 1,2-dihydro-6-oxo-6H-pyrrolo[3,2,1-ij]quinoline which are useful as antimicrobial agents or as intermediates for the preparation of antimicrobial agents.

Also, U.S. Pat. Nos. 3,896,131, 3,985,882, 3,969,463, 4,001,243 and 4,014,877 to Gerster et al disclose 6,7-dihydro-1-oxo-1H, 5H-benzo[ij]quinolizine derivatives having antimicrobial activities.

However, the β-lactam derivatives of the present invention are structurally different from these quinoline and quinolizine compounds. Further, the β-lactam derivatives of the present invention have a potent antimicrobial activity against various bacteria, especially Pseudomonas aeruginosa.

SUMMARY OF THE INVENTION

Accordingly, it is one object of the present invention to provide a β-lactam series compound having high antimicrobial effects and low toxicity.

It is another object of the present invention to provide a pharmaceutical composition comprising these β-lactam series compounds or pharmaceutically acceptable salts thereof.

Still another object of the present invention is to provide an antimicrobial agent which is particularly effective against bacteria which are resistant to streptomycin, ampicillin and/or tetracyclin.

Still another object of the present invention is to provide a process for preparing β-lactam series compounds derived from penicillanic acid, cephalasporic acid and cephalaglycine derivatives.

The present invention provides antimicrobial agents (as well as anticancer and antiviral agents) represented by the following formula (I):

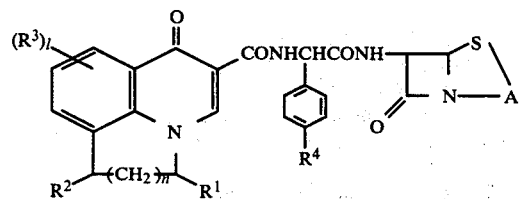

wherein $R^1$ represents a hydrogen atom or a lower alkyl group; $R^2$ represents a hydrogen atom; $R^3$ represents a halogen atom, a nitro group, an amino group, a hydroxy group, a lower alkyl group, a lower alkoxy group, a lower alkanoylamino group, a lower alkanesulfonyloxy group or a group represented by the formula

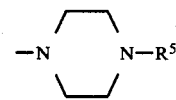

where $R^5$ represents a hydrogen atom, a lower alkanoyl group, or a lower alkanesulfonyl group; $R^4$ represents a hydrogen atom or a hydroxy group; n is an integer of 0 or 1; l is 0, 1 or 2; and A represents —C(CH$_3$)$_2$—CH(COOH)— or —CH$_2$C(CH$_2$R$^6$)=C(COOH)— where $R^6$ represents a lower alkanoyloxy group, a group represented by the formula

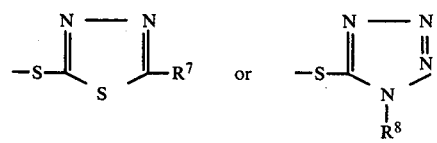

where $R^7$ and $R^8$ each represents a lower alkyl group, and when n is 0, $R^1$ and $R^2$ can combine to form a cyclohexane ring together with the carbon atoms to which they are attached, and pharmaceutically acceptable salts thereof as well as a method for preparing the same.

DETAILED DESCRIPTION OF THE INVENTION

The term "halogen" as used herein includes a chlorine atom, a bromine atom, an iodine atom and a fluorine atom.

The term "lower alkyl" as used herein refers to a straight or branched chain alkyl group having 1 to 4 carbon atoms such as methyl, ethyl, propyl, isopropyl, butyl, tertbutyl groups, etc.

The term "lower alkoxy" as used herein refers to a straight or branched alkoxy group having 1 to 4 carbon atoms such as methoxy, ethoxy, propoxy, isopropoxy, butoxy, tertbutoxy groups and the like.

The term "lower alkanoylamino" as used herein refers to a straight or branched alkanoylamino group having 1 to 4 carbon atoms such as a formylamino group, an acetylamino group, a propanoylamino group, a butanoylamino group, an isobutanoylamino group and the like.

The term "lower alkanesulfonyloxy" as used herein refers to a straight or branched alkanesulfonyloxy group having 1 to 4 carbon atoms such as a methanesulfonyloxy group, an ethanesulfonyloxy group, a propanesulfonyloxy group, an isopropanesulfonyloxy group, a butanesulfonyloxy group, a tert-butanesulfonyloxy group and the like.

The term "lower alkanoyl" as used herein refers to a straight or branched alkanoyl groups having 1 to 4 carbon atoms such as a formyl group, an acetyl group, a propionyl group, a butanoyl group, an isobutanoyl group and the like.

The term "lower alkanesulfonyl" as used herein refers to a straight or branched alkanesulfonyl group having 1 to 4 carbon atoms such as a methanesulfonyl group, an ethanesulfonyl group, a propanesulfonyl group, an isopropanesulfonyl group, a butanesulfonyl group, a tert-butanesulfonyl group and the like.

The term "lower alkanoyloxy" as used herein refers to a straight or branched alkanoyloxy group having 1 to 4 carbon atoms such as a formyloxy group, an acetyloxy group, a propanoyloxy group, a butanoyloxy group, an isobutanoyloxy group and the like.

The β-lactam compounds represented by the formula (I) above are novel compounds and these compounds as well as the pharmaceutically acceptable salts thereof exhibit excellent antimicrobial activity both on gram positive and gram negative bacteria and thus are useful as antibacterial agents.

The compounds of this invention are particularly effective on bacteria belonging to the genera Streptococcus, Pseudomonas, Enterobacter, etc., and exhibit potent antibacterial activity on those bacteria which are resistant to streptomycin, ampicillin and/or tetracyclin.

Representative examples of the compounds of this invention include the following compounds. The list is provided for illustration only and is by no means intended to limit this invention:

6-[2-(7a,8,9,10,11,11a-Hexahydro-4-oxo-4H-pyrido[3,2,1-jk]carbazole-5-carboxamido)-2-phenylacetamido]-3,3-dimethyl-7-oxo-4-thia-1-azabicyclo[3,2,0]heptane-2-carboxylic acid 6-[2-(2-Methyl-7a,8,9,10,11,11a-hexahydro-4-oxo-4H-pyrido[3,2,1-jk]carbazole-5-carboxamido]-3,3-dimethyl-7-oxo-4-thia-1-azabicyclo[3,2,0]heptane-2-carboxylic acid 6-[2-(3-Nitro-7a,8,9,10,11,11a-hexahydro-4-oxo-4H-pyrido[3,2,1-jk]carbazole-5-carboxamido)-2-phenylacetamido]-3,3-dimethyl-7-oxo-4-thia-1-azabicyclo[3,2,0]heptane-2-carboxylic acid 6-[2-(2-Acetylamino-7a,8,9,10,11,11a-hexahydro-4-oxo-4H-pyrido[3,2,1-jk]carbazole-5-carboxamido)-2-phenylacetamido]-3,3-dimethyl-7-oxo-4-thia-1-azabicyclo[3,2,0]heptane-2-carboxylic acid 6-[2-(2-Fluoro-7a,8,9,10,11,11a-hexahydro-4-oxo-4H-pyrido[3,2,1-jk]carbazole-5-carboxamido)-2-phenylacetamido]-3,3-dimethyl-7-oxo-4-thia-1-azabicyclo[3,2,0]heptane-2-carboxylic acid 6-[2-(1,3-Dichloro-7a,8,9,10,11,11a-hexahydro-4-oxo-4H-pyrido[3,2,1-jk]carbazole-5-carboxamido]-3,3-dimethyl-7-oxo-4-thia-1-azabicyclo[3,2,0]heptane-2-carboxylic acid 6-[2-(1-Fluoro-7a,8,9,10,11,11a-hexahydro-4-oxo-4H-pyrido[3,2,1-jk]carbazole-5-carboxamido)-2-phenylacetamido]-3,3-dimethyl-7-oxo-4-thia-1-azabicyclo[3,2,0]heptane-2- carboxylic acid 6-[2-(3-Fluoro-7a,8,9,10,11,11a-hexahydro-4-oxo-4H-pyrido[3,2,1-jk]carbazole-5-carboxamido)-2-phenylacetamido]-3,3-dimethyl-7-oxo-4-thia-1-azabicyclo[3,2,0]heptane-2-carboxylic acid 6-[2-(1-Chloro-7a,8,9,10,11,11a-hexahydro-4-oxo-4H-pyrido[3,2,1-jk]carbazole-5-carboxamido)-2-phenylacetamido]-3,3-dimethyl-7-oxo-4-thia-1-azabicyclo[3,2,0]heptane-2-carboxylic acid 6-[2-(1-Methyl-7a,8,9,10,11,11a-hexahydro-4-oxo-4H-pyrido[3,2,1-jk]carbazole-5-carboxamido)-2-phenylacetamido]-3,3-dimethyl-7-oxo-4-thia-1-azabicyclo[3,2,0]heptane-2-carboxylic acid 6-[2-(1-Acetylamino-7a,8,9,10,11,11a-hexahydro-4-oxo-4H-pyrido[3,2,1-jk]carbazole-5-carboxamido)-2-phenylacetamido]-3,3-dimethyl-7-oxo-4-thia-1-azabicyclo[3,2,0]heptane-2-carboxylic acid 8-[2-(1-Hydroxy-7a,8,9,10,11,11a-hexahydro-4-oxo-pyrido[3,2,1-jk]carbazole-5-carboxamido)-2-phenylacetamido]-3,3-dimethyl-7-oxo-4-thia-1-azabicyclo[3,2,0]heptane-2-carboxylic acid 6-[2-(2-Hydroxy-7a,8,9,10,11,11a-hexahydro-4-oxo-4H-pyrido[3,2,1-jk]carbazole-5-carboxamido)-2-phenylacetamido]-3,3-dimethyl-7-oxo-4-thia-1-azabicyclo[3,2,0]heptane-2-carboxylic acid 6-[2-(2-Methoxy-7a,8,9,10,11,11a-hexahydro-4-oxo-4H-pyrido[3,2,1-jk]carbazole-5-carboxamido)-2-phenylacetamido]-3,3-dimethyl-7-oxo-4-thia-1-azabicyclo[3,2,0]heptane-2-carboxylic acid 6-[2-(1,2-Dimethoxy-7a,8,9,10,11,11a-hexahydro-4-oxo-4H-pyrido[3,2,1-jk]carbazole-5-carboxamido)-2-phenylacetamido]-3,3-dimethyl-7-oxo-4-thia-1-azabicyclo[3,2,0]heptane-2-carboxylic acid 6-[2-(1,3-Dimethyl-7a,8,9,10,11,11a-hexahydro-4-oxo-4H-pyrido[3,2,1-jk]carbazole-5-carboxamido)-2-phenylacetamido]-3,3-dimethyl-7-oxo-4-thia-1-azabicyclo[3,2,0]heptane-2-carboxylic acid 6-[2-(3-Amino-7a,8,9,10,11,11a-hexahydro-4-oxo-4H-pyrido[3,2,1-jk]carbazole-5-carboxamido)-2-phenylacetamido]-3,3-dimethyl-7-oxo-4-thia-1-azabicyclo[3,2,0]heptane-2-carboxylic acid.

6-[2-(7a,8,9,10,11,11a-Hexahydro-4-oxo-4H-pyrido[3,2,1-jk]carbazole-5-carboxamido)-2-(4-hydroxy)phenylacetamido]-3,3-dimethyl-7-oxo-4-thia-1-azabicyclo[3,2,0]heptane-2-carboxylic acid 6-[2-(2-Fluoro-7a,8,9,10,11,11a-hexahydro-4-oxo-4H-pyrido[3,2,1-jk]carbazole-5-carboxamido)-2-(4-hydroxy)phenylacetamido]-3,3-dimethyl-7-oxo-4-thia-1-azabicyclo[3,2,0]heptane-2-carboxylic acid 6-[2-(1-Chloro-7a,8,9,10,11,11a-hexahydro-4-oxo-4H-pyrido[3,2,1-jk]carbazole-5-carboxamido)-2-(4-hydroxy)phenylacetamido]-3,3-dimethyl-7-oxo-4-thia-1-azabicyclo[3,2,0]heptane-2-carboxylic acid 6-[2-(2-Methyl-7a,8,9,10,11,11a-hexahydro-4-oxo-4H-pyrido[3,2,1-jk]carbazole-5-carboxamido)-2-(4-hydroxy)phenylacetamido]-3,3-dimethyl-7-oxo-4-thia-1-azabicyclo[3,2,0]heptane-2-carboxylic acid 6-[2-(3-Nitro-7a,8,9,10,11,11a-hexahydro-4-oxo-4H-pyrido[3,2,1-jk]carbazole-5-carboxamido)-2-(4-hydroxy)phenylacetamido]-3,3-dimethyl-7-oxo-4-thia-1-azabicyclo[3,2,0]heptane-2-carboxylic acid 6-[2-(1-Hydroxy-7a,8,9,10,11,11a-hexahydro-4-oxo-4H-pyrido[3,2,1-jk]carbazole-5-carboxamido)-2-(4-hydroxy)phenylacetamido]-3,3-dimethyl-7-oxo-4-thia-1-azabicyclo[3,2,0]heptane-2-carboxylic acid 6-[2-(2-Methoxy-7a,8,9,10,11,11a-hexahydro-4-oxo-4H-pyrido[3,2,1-jk]carbazole-5-carboxamido)-2-(4-hydroxy)phenylacetamido]-3,3-dimethyl-7-oxo-4-thia-1-azabicyclo[3,2,0]heptane-2-carboxylic acid 6-{2-[1-(1-Piperazinyl)-7a,8,9,10,11,11a-hexahydro-4H-pyrido[3,2,1-jk]carbazole-4-oxo-5-carboxamido]-2-phenylacetamido}-3,3-dimethyl-7-oxo-4-thia-1-azabicyclo[3,2,0]heptane-2-carboxylic acid 6-{2-[1-(1-Piperazinyl)-7a,8,9,10,11,11a-hexahydro-4H-pyrido[3,2,1-jk]carbazole-4-oxo-5-carboxamido]-2-(4-hydroxyphenyl)acetamido}-3,3-dimethyl-7-oxo-4-thia-1-azabicyclo[3,2,0]heptane-2-carboxylic acid 6-{2-[3-(1-Piperazinyl)-7a,8,9,10,11,11a-hexahydro-4H-pyrido[3,2,1-jk]carbazole-4-oxo-5-carboxamido]-2-phenylacetamido}-3,3-dimethyl-7-oxo-4-thia-1-azabicyclo[3,2,0]heptane-2-carboxylic acid 6-{2-[1-(4-Acetyl-1-piperazinyl)-7a,8,9,10,11,11a-hexahydro-4H-pyrido[3,2,1-jk]carbazole-4-oxo-5-carboxamido]-2-phenylacetamido}-3,3-dimethyl-7- oxo-4-thia-1-azabicyclo[3,2,0]heptane-2-carboxylic acid

6-{2-[1-(1-Methanesulfonyl-1-piperazinyl)-7a,8,9,10,11,11a-hexahydro-4H-pyrido[3,2,1-jk]carbazole-4-oxo-5-carboxamido]-2-phenylacetamido}-3,3-dimethyl-7-oxo-4-thia-1-azabicyclo[3,2,0]heptane-2-carboxylic acid 6-[2-(1-Methanesulfonyloxy-7a,8,9,10,11,11a-hexahydro-4H-pyrido[3,2,1jk]carbazole-4-oxo-5-carboxamido]-2-phenylacetamido]-3,3-dimethyl-7-oxo-4-thia-1-azabicyclo[3,2,0]heptane-2-carboxylic acid 6-[2-(2-Fluoro-1-methyl-7a,8,9,10,11,11a-hexahydro-4H-pyrido[3,2,1-jk]carbazole-4-oxo-5-carboxamido)-2-phenylacetamido]-3,3-dimethyl-7-oxo-4-thia-1-azabicyclo[3,2,0]heptane-2-carboxylic acid 7-[2-(7a,8,9,10,11,11a-Hexahydro-4-oxo-pyrido[3,2,1-jk]carbazole-5-carboxamido]-2-phenylacetamido]-3-(acetyloxymethyl)-8-oxo-5-thia-1-azabicyclo[4,2,0]oct-2-ene-2-carboxylic acid 7-[2-(7a,8,9,10,11,11a-Hexahydro-4-oxo-4-H-pyrido[3,2,1-jk]carbazole-5-carboxamido)-2-phenylacetamido]-3-[2-(5-methyl-1,3,4-thiadiazole)thiomethyl]-8-oxo-5-thia-1-azabicyclo[4,2,0]oct-2-ene-2-carboxylic acid 7-[2-(2-Methyl-7a,8,9,10,11,11a-hexahydro-4-oxo-4H-pyrido[3,2,1-jk]carbazole-5-carboxamido)-2-phenylacetamido]-3-[5-(1-methyl-1,2,3,4-tetrazole)thiomethyl]-8-oxo-5-thia-1-azabicyclo[4,2,-0]oct-2-ene-2-carboxylic acid 7-[2-(2-Fluoro-7a,8,9,10,11,11a-hexahydro-4-oxo-4H--pyrido[3,2,1-jk]carbazole-5-carboxamido)-2-phenylacetamido]-3-(1-pyridylmethyl)-8-oxo-5-thia-1-azabicyclo[4,2,0]oct-2-ene-2-carboxylic acid 7-[2-(3-Nitro-7a,8,9,10,11,11a-hexahydro-4-oxo-4H-pyrido[3,2,1-jk]carbazole-5-carboxamido)-2-phenylacetamido]-3-(acetyloxymethyl)-8-oxo-5-thia-1-azabicyclo[4,2,0]-oct-2-ene-2-carboxylic acid 7-[2-(7a,8,9,10,11,11a-Hexahydro-4-oxo-4-H-pyrido[3,2,1-jk]carbazole-5-carboxamido)-2-(4-hydroxy)phenylacetamido]-3-[2-(5-methyl-1,3,4-thiadiazole)thiomethyl]-8-oxo-5-thia-1-azabicyclo[4,2,0]oct-2-ene-2-carboxylic acid 7-[2-(2-Acetylamido-7a,8,9,10,11,11a-hexahydro-4-oxo-4-H-pyrido[3,2,1-jk]carbazole-5-carboxamido)-2-(4-hydroxy)phenylacetamido]-3-(acetyloxymethyl)-8-oxo-5-thia-1-azabicyclo[4,2,0]oct-2-ene-2-carboxylic acid 7-[2-(2-Methoxy-7a,8,9,10,11,11a-hexahydro-4-oxo-4H-pyrido[3,2,1-jk]carbazole-5-carboxamido)-2-(4-hydroxy)phenylacetamido]-3-[5-(1-methyl-1,2,3,4-tetrazole)thiomethyl]-8-oxo-5-thia-1-azabicyclo[4,2,-0]oct-2-ene-2-carboxylic acid 7-{2-[1-(1-Piperazinyl)-7a,8,9,10,11,11a-hexahydro-4H-pyrido[3,2,1-jk]carbazole-4-oxo-5-carboxamido]-2-phenylacetamido}-3-(acetyloxymethyl)-8-oxo-5-thia-1-azabicyclo[4,2,0]oct-2-ene-2-carboxylic acid 6-[2-(9-Chloro-6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid 6-[2-(8-Chloro-6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxlic acid 6-[2-(8,10-Dichloro-6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid 6-[2-(6,7-Dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid 6-[2-(9-Fluoro-6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid 6-[2-(9-Methoxy-6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid 6-[2-(10-Methoxy-6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid 6-[2-(8-Methyl,6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid 6-[2-(9-Methyl-6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid 6-[2-(8-Amino-6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid 6-[2-(9-Nitro-6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid 6-[2-(8-Acetylamino-6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid 6-[2-(9-Acetylamino-6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid 6-[2-(9-Hydroxy-6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid 6-[2-(10-Hydroxy-6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid 6-[2-(6,7-Dihydro-1-oxo-1H,5H-benzo[ij]quinolizine-2-carboxamido)-2-(4-hydroxy)phenylacetamido]-3,3-dimethyl-7-oxo-4-thia-1-azabicyclo[3,2,0]heptane-2-carboxylic acid 6-[2-(9-Chloro-6,7-dihydro-1-oxo-1H,5H-benzo[ij]quinolizine-2-carboxamido)-2-(4-hydroxy)phenylacetamido]-3,3-dimethyl-7-oxo-4-thia-1-azabicyclo[3,2,0]heptane-2-carboxylic acid 6-[2-(8-Fluoro-6,7-dihydro-1-oxo-1H,5H-benzo[ij]quinolizine-2-carboxamido)-2-(4-hydroxy)phenylacetamido]-3,3-dimethyl-7-oxo-4-thia-1-azabicyclo[3,2,0]heptane-2-carboxylic acid 6-[2-(9-Fluoro-6,7-dihydro-1-oxo-1H,5H-benzo[ij]quinolizine-2-carboxamido)-2-(4-hydroxy)phenylacetamido]-3,3-dimethyl-7-oxo-4-thia-1-azabicyclo[3,2,0]heptane-2-carboxylic acid 6-[2-(10-Fluoro-6,7-dihydro-1-oxo-1H,5H-benzo[ij]quinolizine-2-carboxamido)-2-(4-hydroxy)phenylacetamido]-3,3-dimethyl-7-oxo-4-thia-1-azabicyclo[3,2,0]heptane-2-carboxylic acid 6-[2-(9-Nitro-6,7-dihydro-1-oxo-1H,5H-benzo[ij]-quinolizine-2-carboxamido)-2-(4-hydroxy)-phenylacetamido]-3,3-dimethyl-7-oxo-4-thia-1-azabicyclo[3,2,0]heptane-2-carboxylic acid 6-[2-(8-Isopropoxy-6,7-dihydro-1-oxo-1H,5H-benzo[ij]-quinolizine-2-carboxamido)-2-phenylacetamido]-3,3-dimethyl-7-oxo-4-thia-1-azabicyclo[3,2,0]heptane-2-carboxylic acid 6-[2-(8-Butyl-6,7-dihydro-1-oxo-1H,5H-benzo[ij]-quinolizine-2-carboxamido)-2-phenylacetamido]-3,3-dimethyl-7-oxo-4-thia-1-azabicyclo[3,2,0]heptane-2-carboxylic acid 6-[2-(10-Butyrylamino-6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid 6-[2-(5-Methyl-6,7-dihydro-1-oxo-1H,5H-benzo[ij]-quinolizine-2-carboxamido)-2-phenylacetamido]-3,3-dimethyl-7-oxo-4-thia-1-azabicyclo[3,2,0]heptane-2-carboxylic acid 6-[2-(5-Methyl-6,7-dihydro-1-oxo-1H,5H-benzo[ij]-quinolizine-2-carboxamido)-2-(4-hydroxy)-phenylacetamido]-3,3-dimethyl-7-oxo-4-thia-1-azabicyclo[3,2,0]heptane-2-carboxylic acid 6-[2-(5-Ethyl-6,7-dihydro-1-oxo-1H,5H-benzo[ij]-quinolizine-2-carboxamido)-2-phenylacetamido]-3,3-dimethyl-7-oxo-4-thia-1-azabicyclo[3,2,0]heptane-2-carboxylic acid 6-[2-(5-Isopropyl-6,7-dihydro-1-oxo-1H,5H-benzo[ij]-quinolizine-2-carboxamido)-2-(4-hydroxy)-phenylacetamido]-3,3-dimethyl-7-oxo-4-thia-1-azabicyclo[3,2,0]heptane-2-carboxylic acid 6-{2-[8-(1-Piperazinyl)-6,7-dihydro-1-oxo-1H,5H-benzo[ij]quinolizine-2-carboxamido]-2-phenylacetamido}-3,3-dimethyl-7-oxo-4-thia-1-azabicyclo[3,2,0]heptane-2-carboxylic acid 6-{2-[8-(1-Peperazinyl)-6,7-dihydro-1-oxo-1H,5H-benzo[ij]quinolizine-2-carboxamido]-2-(4-hydroxy)-phenylacetamido}-3,3-dimethyl-7-oxo-4-thia-1-azabicyclo[3,2,0]heptane-2-carboxylic acid 6-{2-[8-(4-Acetyl-1-piperazinyl)-6,7-dihydro-1-oxo-1H,5H-benzo[ij]quinolizine-2-carboxamido]-2-phenylacetamido}-3,3-dimethyl-7-oxo-4-thia-1-azabicyclo[3,2,0]heptane-2-carboxylic acid 6-{2-[8-(4-Formyl-1-piperazinyl)-6,7-dihydro-1-oxo-1H,5H-benzo[ij]quinolizine-2-carboxamido]-2-(4-hydroxy)phenylacetamido}-3,3-dimethyl-7-oxo-4-thia-1-azabicyclo[3,2,0]heptane-2-carboxylic acid 6-{2-[8-(4-Methanesulfonyl-1-piperazinyl)-6,7-dihydro-1-oxo-1H,5H-benzo[ij]quinolizine-2-carboxamido]-2-phenylacetamido}-3,3-dimethyl-7-oxo-4-thia-1-azabicyclo[3,2,0]heptane-2-carboxylic acid 6-{2-[8-(4-Ethanesulfonyl-1-piperazinyl)-6,7-dihydro-1-oxo-1H,5H-benzo[ij]quinolizine-2-carboxamido]2-(4-hydroxy)phenylacetamido}-3,3-dimethyl-7-oxo-4-thia-1-azabicyclo[3,2,0]heptane-2-carboxylic acid 6-{2-[8-(1-Piperazinyl)-5-methyl-6,7-dihydro-1-oxo-1H,5H-benzo[ij]quinoline-2-carboxamido]-2-phenylacetamido}-3,3-dimethyl-7-oxo-4-thia-1-azabicyclo[3,2,0]heptane-2-carboxylic acid 6-{2-[8-(1-Piperazinyl)-5-methyl-6,7-dihydro-1-oxo-1H,5H-benzo[ij]quinolizine-2-carboxamido[-2-(4-hydroxy)phenylacetamido}-3,3-dimethyl-7-oxo-4-thia-1-azabicyclo[3,2,0]heptane-2-carboxylic acid 6-[2-(9-Fluoro-5-methyl-6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid 6-[2-(9-Methoxy-5-methyl-6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid 6-[2-(5,10-dimethyl-6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid 6-[2-(8-Chloro-5-methyl-6,7-dihydro-1-oxo-1H,5H-benzo[ij]quinolizine-2-carboxamido)-2-(4-hydroxy)-phenylacetamido]-3,3-dimethyl-7-oxo-4-thia-1-azabicyclo[3,2,0]heptane-2-carboxylic acid 6-{2-[9-(1-Piperazinyl)-6,7-dihydro-1-oxo-1H,5H-benzo[ij]quinolizine-2-carboxamido]-2-phenylacetamido}-3,3-dimethyl-7-oxo-4-thia-1-azabicyclo[3,2,0]heptane-2-carboxylic acid 6-{2-[10-(4-Acetyl-1-piperazinyl)-6,7-dihydro-1-oxo-1H,5H-benzo[ij]quinolizine-2-carboxamido]-2-phenylacetamido}-3,3-dimethyl-7-oxo-4-thia-1-azabicyclo[3,2,0]heptane-2-carboxylic acid 6-[2-(8-Methanesulfonyloxy-6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid 7-[2-(6,7-Dihydro-1-oxo-1H,5H-benzo[ij]quinolizine-2-carboxamido)-2-phenylacetamido]-3-(acetyloxymethyl)-8-oxo-5-thia-1-azabicyclo[4,2,0]oct-2-ene-2-carboxylic acid 7-[2-(5-Methyl-6,7-dihydro-1-oxo-1H,5H-benzo[ij]-quinolizine-2-carboxamido)-2-phenylacetamido]-3-(acetyloxymethyl)-8-oxo-5-thia-1-azabicyclo[4,2,0]oct-2-ene-2-carboxylic acid 7-[2-(6,7-Dihydro-1-oxo-1H,5H-benzo[ij]quinolizine-2-carboxamido)-2-phenylacetamido]-3-[2-(5-methyl-1,3,4-thiadiazole)thiomethyl]-8-oxo-5-thia-1-azabicyclo[4,2,0]oct-2-ene-2-carboxylic acid 7-[2-(5-Methyl-6,7-dihydro-1-oxo-1H,5H-benzo[ij]quinolizine-2-carboxamido)-2-phenylacetamido]-3-[5-(1-methyl-1,2,3,4-tetrazole)thiomethyl]-8-oxo-5-thia-1-azabicyclo[4,2,0]oct-2-ene-2-carboxylic acid 7-[2-(6,7-Dihydro-1-oxo-1H,5H-benzo[ij]quinolizine-2-carboxamido)-2-(4-hydroxy)phenylacetamido]-3-(acetyloxymethyl)-8-oxo-5-thia-1-azabicyclo[4,2,0]oct-2-ene-2-carboxylic acid 7-[2-(5-Methyl-6,7-dihydro-1-oxo-1H,5H-benzo[ij]-quinolizine-2-carboxamido)-2-(4-hydroxy)-phenylacetamido]-3-[2-(5-methyl-1,3,4-thiadiazole)-thiomethyl]-8-oxo-5-thia-1-azabicyclo[4,2,0]oct-2-ene-2-carboxylic acid 7-[2-(6,7-Dihydro-1-oxo-1H,5H-benzo[ij]quinolizine-2-carboxamido)-2-(4-hydroxy)phenylacetamido]-3-[5-(1-methyl-1,2,3,4-tetrazole)thiomethyl]-8-oxo-5-thia-1-azabicyclo[4,2,0]oct-2-ene-2-carboxylic acid 7-[2-(9-Fluoro-6,7-dihydro-1-oxo-1H,5H-benzo[ij]-quinolizine-2-carboxamido)-2-phenylacetamido]-3-(acetyloxymethyl)-8-oxo-5-thia-1-azabicyclo[4,2,0]oct-2-ene-2-carboxylic acid 7-[2-(10-Methoxy-6,7-dihydro-1-oxo-1H,5H-benzo[ij]quinolizine-2-carboxamido)-2-phenylacetamido]-3-[2-(5-methyl-1,3,4-thiadiazole)thiomethyl]-8-oxo-5-thia-1-azabicyclo[4,2,0]oct-2-ene-2-carboxylic acid 7-[2-(8-Methyl-6,7-dihydro-1-oxo-1H,5H-benzo[ij]quinolizine-2-carboxamido)-2-phenylacetamido]-3-[5-(1-methyl-1,2,3,4-tetrazole)thiomethyl]-8-oxo-5-thia-1-azabicyclo[4,2,0]oct-2-ene-2-carboxylic acid 7-[2-(9-Hydroxy-6,7-dihydro-1-oxo-1H,5H-benzo[ij]quinolizine-2-carboxamido)-2-phenylacetamido]-3-[2-(5-methyl-1,3,4-thiadiazole)thiomethyl]-8-oxo-5-thia-1-azabicyclo[4,2,0]oct-2-ene-2-carboxylic acid 7-[2-(9-Chloro-5-methyl-6,7-dihydro-1-oxo-1H,5H-benzo[ij]quinolizine-2-carboxamido)-2-(4-hydroxy)-phenylacetamido]-3-(acetyloxymethyl)-8-oxo-5-thia-1-azabicyclo[4,2,0]oct-2-ene-2-carboxylic acid 7-{2-[8-(1-Piperazinyl)-6,7-dihydro-1-oxo-1H,5H-benzo[ij]quinolizine-2-carboxamido]-2-phenylacetamido}-3-[2-(5-methyl-1,3,4-thiadiazole)-thiomethyl]-8-oxo-5-thia-1-azabicyclo[4,2,0]oct-2-ene-2-carboxylic acid 7-{2-[8-(4-Acetyl-1-piperazinyl)-6,7-dihydro-1-oxo-1H,5H-benzo[ij]quinolizine-2-carboxamido]-2-phenylacetamido}-3-(acetyloxymethyl)-8-oxo-5-thia-1-azabicyclo[4,2,0]oct-2-ene-2-carboxylic acid 7-[2-(8-Methanesulfonyloxy-6,7-dihydro-1-oxo-1H,5H-benzo[ij]quinolizine-2-carboxamido)-2-phenylacetamido]-3-[5-(1-methyl-1,2,3,4-tetrazole)-thiomethyl]-8-oxo-5-thia-1-azabicyclo[4,2,0]oct-2-ene-2-carboxylic acid 6-[2-(8-Fluoro-1,2-dihydro-6-oxo-6H-pyrrolo[3,2,1-ij]quinoline-5-carboxamido)-2-phenylacetamido]-3,3-dimethyl-7-oxo-4-thia-1-azabicyclo[3,2,0]heptane-2-carboxylic acid 6-[2-(8-Methyl-1,2-dihydro-6-oxo-6H-pyrrolo[3,2,1-ij]quinoline-5-carboxamido)-2-phenylacetamido]-3,3-dimethyl-7-oxo-4-thia-1-azabicyclo[3,2,0]heptane-2-carboxylic acid 6-[2-(9-Chloro-1,2-dihydro-6-oxo-6H-pyrrolo[3,2,1-ij]quinoline-5-carboxamido)-2-phenylacetamido]-3,3-dimethyl-7-oxo-4-thia-1-azabicyclo[3,2,0]heptane-2-carboxylic acid 6-[2-(2,9-Dimethyl-1,2-dihydro-6-oxo-6H-pyrrolo[3,2,1-ij]quinoline-5-carboxamido)-2-phenylacetamido]-3,3-dimethyl-7-oxo-4-thia-1-azabicyclo[3,2,0]heptane-2-carboxylic acid 6-[2-(7-Nitro-1,2-dihydro-6-oxo-6H-pyrrolo[3,2,1-ij]quinoline-5-carboxamido)-2-phenylacetamido]-3,3-dimethyl-7-oxo-4-thia-1-azabicyclo[3,2,0]heptane-2-carboxylic acid 6-[2-(8-Methoxy-1,2-dihydro-6-oxo-6H-pyrrolo[3,2,1-ij]quinoline-5-carboxamido)-2-phenylacetamido]-3,3-dimethyl-7-oxo-4-thia-1-azabicyclo[3,2,0]heptane-2-carboxylic acid 6-[2-(8-Hydroxy-1,2-dihydro-6-oxo-6H-pyrrolo[3,2,1-ij]quinoline-5-carboxamido)-2-phenylacetamido]-3,3-dimethyl-7-oxo-4-thia-1-azabicyclo[3,2,0]heptane-2-carboxylic acid 6-[2-(1,2-Dihydro-6-oxo-6H-pyrrolo[3,2,1-ij]quinoline-5-carboxamido)-2-(4-hydroxy)phenylacetamido]-3,3-dimethyl-7-oxo-4-thia-1-azabicyclo[3,2,0]heptane-2-carboxylic acid 6-[2-(8-Fluoro-1,2-dihydro-6-oxo-6H-pyrrolo[3,2,1-ij]quinoline-5-carboxamido)-2-(4-hydroxy)-phenylacetamido]-3,3-dimethyl-7-oxo-4-thia-1-azabicyclo[3,2,0]heptane-2-carboxylic acid 6-[2-(1,2-Dihydro-6-oxo-6H-pyrrolo[3,2,1-ij]quinoline-5-carboxamido)-2-phenylacetamido]-3,3-dimethyl-7-oxo-4-thia-1-azabicyclo[3,2,0]heptane-2-carboxylic acid 6-[2-(8-Chloro-1,2-dihydro-6-oxo-6H-pyrrolo[3,2,1-ij]quinoline-5-carboxamido)-2-phenylacetamido]-3,3-dimethyl-7-oxo-4-thia-1-azabicyclo[3,2,0]heptane-2-carboxylic acid 6-[2-(7-Amino-1,2-dihydro-6-oxo-6H-pyrrolo[3,2,1-ij]quinoline-5-carboxamido)-2-phenylacetamido]-3,3-dimethyl-7-oxo-4-thia-1-azabicyclo[3,2,0]heptane-2-carboxylic acid 6-[2-(7-Acetylamino-1,2-dihydro-6-oxo-6H-pyrrolo[3,2,1-ij]quinoline-5-carboxamido)-2-(4-hyroxy)-phenylacetamido]-3,3-dimethyl-7-oxo-4-thia-1-azabicyclo[3,2,0]heptane-2-carboxylic acid 6-[2-(8-Ethoxy-1,2-dihydro-6-oxo-6H-pyrrolo-[3,2,1-ij]quinoline-5-carboxamido)-2-(4-hydroxy)-phenylacetamido]-3,3-dimethyl-7-oxo-4-thia-1-azabicyclo[3,2,0]heptane-2-carboxylic acid 6-[2-(7-Ethyl-1,2-dihydro-6-oxo-6H-pyrrolo[3,2,1-ij]quinoline-5-carboxamido)-2-(4-hydroxy)-phenylacetamido]-3,3-dimethyl-7-oxo-4-thia-1-azabicyclo[3,2,0]heptane-2-carboxylic acid 6-{2-[9-(1-Piperazinyl)-6-oxo-1,2-dihydro-6H-pyrrolo[3,2,1-ij]quinoline-5-carboxamido]-2-phenylacetamido}-3,3-dimethyl-7-oxo-4-thia-1-azabicyclo[3,2,0]heptane-2-carboxylic acid 6-{2-[9-(1-Piperazinyl)-2-methyl-6-oxo-1,2-dihydro-6H-pyrrolo[3,2,1-ij]quinoline-5-carboxamido]-2-phenylacetamido}-3,3-dimethyl-7-oxo-4-thia-1-azabicyclo[3,2,0]heptane-2-carboxylic acid 6-{2-[9-(1-Piperazinyl)-2-ethyl-6-oxo-1,2-dihydro-6H-pyrrolo[3,2,1-ij]quinoline-5-carboxamido]-2-phenylacetamido}-3,3-dimethyl-7-oxo-4-thia-1-azabicyclo[3,2,0]heptane-2-carboxylic acid 6-{2-[9-(1-Piperazinyl)-6-oxo-1,2-dihydro-6H-pyrrolo[3,2,1-ij]quinoline-5-carboxamido]-2-(4-hydroxy)phenylacetamido}-3,3-dimethyl-7-oxo-4-thia-1-azabicyclo[3,2,0]heptane-2-carboxylic acid 6-{2-[9-(1-Piperazinyl)-2-methyl-6-oxo-1,2-dihydro-6H-pyrrolo[3,2,1-ij]quinoline-5-carboxamido]-2-(4-hydroxy)phenylacetamido}-3,3-dimethyl-7-oxo-4-thia-1-azabicyclo[3,2,0]heptane-2-carboxylic acid 6-{2-[8-(1-Piperazinyl)-6-oxo-1,2-dihydro-6H-pyrrolo[3,2,1-ij]quinoline-5-carboxamido]-2-phenylacetamido}-3,3-dimethyl-7-oxo-4-thia-1-azabicyclo[3,2,0]heptane-2-carboxylic acid 6-[2-(9-Ethanesulfonyloxy-6-oxo-1,2-dihydro-6H-pyrrolo[3,2,1-ij]quinoline-5-carboxamido)-2-phenylacetamido]-3,3-dimethyl-7-oxo-4-thia-1-azabicyclo[3,2,0]heptane-2-carboxylic acid 6-[2-(2-Methyl-1,2-dihydro-6-oxo-6H-pyrrolo[3,2,1-ij]quinoline-5-carboxamido)-2-phenylacetamido]-3,3-dimethyl-7-oxo-4-thia-1-azabicyclo[3,2,0]heptane-2-carboxylic acid 6-[2-(8-Fluoro-2-methyl-1,2-dihydro-6-oxo-6H-pyrrolo[3,2,1-ij]quinoline-5-carboxamido)-2-phenylacetamido]-3,3-dimethyl-7-oxo-4-thia-1-azabicyclo[3,2,0]heptane-2-carboxylic acid 6-[2-(2-Methyl-1,2-dihydro-6-oxo-6H-pyrrolo[3,2,1-ij]quinoline-5-carboxamido)-2-(4-hydroxy)-phenylacetamido]-3,3-dimethyl-7-oxo-4-thia-1-azabicyclo[3,2,0]heptane-2-carboxylic acid 6-{2-[9-(4-Acetyl-1-piperazinyl)-6-oxo-1,2-dihydro-6H-pyrrolo[3,2,1-ij]quinoline-5-carboxyamido]-2-phenylacetamido}-3,3-dimethyl-7-oxo-4-thia-1-azabicyclo[3,2,0]heptane-2-carboxylic acid 6-{2-[9-(4-Ethanesulfonyl-1-piperazinyl-2-methyl-6-oxo-1,2-dihydro-6H-pyrrolo[3,2,1-ij]quinoline-5-carboxamido]2-phenylacetamido}-3,3-dimethyl-7-oxo-4-thia-1-azabicyclo[3,2,0]heptane-2-carboxylic acid 6-[2-(8-Chloro-2-methyl-1,2-dihydro-6-oxo-6H pyrrolo[3,2,1-ij]quinoline-5-carboxamido)-2(4-hydroxy)phenylacetamido]-3,3-dimethyl-7-oxo-4-thia-1-azabicyclo[3,2,0]heptane-2-carboxylic acid 6-{2-[9-(4-Formyl-1-piperazinyl)-6-oxo-1,2-dihydro-6H-pyrrolo[3,2,1-ij]quinoline-5-carboxamido]-2-

(4-hydroxy)phenylacetamido]-3,3-dimethyl-7-oxo-4-thia-1-azabicyclo[3,2,0]heptane-2-carboxylic acid 6-[2-(8-Fluoro-7-methyl-6-oxo-1,2-dihydro-6H-pyrrolo[3,2,1-ij]quinoline-5-carboxamido)-2-phenylacetamido]-3,3-dimethyl-7-oxo-4-thia-1-azabicyclo[3,2,0]heptane-2-carboxylic acid 7-[2-(1,2-Dihydro-6-oxo-6H-pyrrolo[3,2,1-ij]quinoline-5-carboxamido)-2-phenylacetamido]-3-(acetyloxymethyl)-8-oxo-5-thia-1-azabicyclo[4,2,0]oct-2-ene-2-carboxylic acid 7-[2-(2-Methyl-1,2-dihydro-6-oxo-6H-pyrrolo [3,2,1-ij]-quinoline-5-carboxamido)-2-(4-hydroxy)-phenylacetamido]-3-[2-(5-methyl-1,3,4-thiadiazole)-thiomethyl]-8-oxo-5-thia-1-azabicyclo[4,2,0]oct-2-ene-2-carboxylic acid 7-[2-(8-Fluoro-2-methyl-1,2-dihydro-6-oxo-6H-pyrrolo[3,2,1-ij]quinoline-5-carboxamido)-2-phenylacetamido]-3-[5-(1-methyl-1,2,3,4-tetrazole)-thiomethyl]-8-oxo-5-thia-1-azabicyclo[4,2,0]oct-2-ene-2-carboxylic acid 7-[2-(7-Nitro-1,2-dihydro-6-oxo-6H-pyrrolo[3,2,1-ij]quinoline-5-carboxamido)-2-phenylacetamido]-3-[2-(5-methyl-1,3,4-thiadiazole)thiomethyl]-8-oxo-5-thia-1-azabicyclo[4,2,0]oct-2-ene-2-carboxylic acid 7-[2-(2-Methyl-1,2-dihydro-6-oxo-6H-pyrrolo[3,2,1-ij]quinoline-5-carboxamido)-2-phenylacetamido]-3-[5-(1-methyl-B 1,2,3,4-tetrazole)thiomethyl]-8-oxo-5-thia-1-azabicyclo[4,2,0]oct-2-ene-2-carboxylic acid 7-[2-(8-Methoxy-1,2-dihydro-6-oxo-6H-pyrrolo[3,2,1-ij]quinoline-5-carboxamido)-2-phenylacetamido]-3-(1-pyridylmethyl)-8-oxo-5-thia-1-azabicyclo[4,2,-0]oct-2-ene-2-carboxylic acid betaine 7-[2-(8-Hydroxy-1,2-dihydro-6-oxo-6H-pyrrolo[3,2,1-ij]quinoline-5-carboxamido)-2-(4-hyroxy)-phenylacetamido]-3-[acetyloxymethyl]-8-oxo-5-thia-1-azabicyclo[4,2,0]oct-2-ene-2-carboxylic acid 7-[2-(7-Acetylamino-1,2-dihydro-6-oxo-6H-pyrrolo[3,2,1-ij]quinoline-5-carboxamido)-2-phenylacetamido]-3-[5-(1-methyl-1,2,3,4-tetrazole)-thiomethyl]-8-oxo-5-thia-1-azabicyclo[4,2,0]oct-2-ene-2-carboxylic acid 7-{2-[9-(1-Piperazinyl)-2-methyl-6-oxo-1,2-dihydro-6H-pyrrolo[3,2,1-ij]quinoline-5-carboxamido]-2-phenylacetamido}-3-(acetyloxymethyl)-8-oxo-5-thia-1-azabicyclo[4,2,0]oct-2-ene-2-carboxylic acid 7-{2-[9-(4-Acetyl-1-piperazinyl)-6-oxo-1,2-dihydro-6H-pyrrolo[3,2,1-ij]quinoline-5-carboxamido]-2-phenylacetamido}-3-[2-(5-methyl-1,3,4-thiadiazole)-thiomethyl]-8-oxo-5-thia-1-azabicyclo[4,2,0]oct-2-ene-2-carboxylic acid 7-{2-[9-(1-Piperazinyl)-6-oxo-1,2-dihydro-6H-pyrrolo[3,2,1-ij]quinoline-5-carboxamido]-2-(4-hydroxy)-phenylacetamido}-3-[5-(1-methyl-1,2,3,4-tetrazole)-thiomethyl]-8-oxo-5-thia-1-azabicyclo[4,2,0]oct-2-ene-2-carboxylic acid The compounds of this invention are penicillanic acid and cephalosporic acid derivatives and can be prepared by various alternative procedures from carboxylic acid group containing compounds represented by the formula (II):

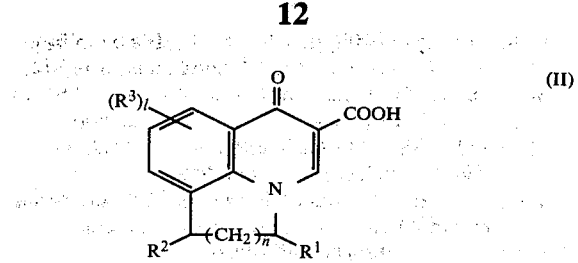

wherein $R^1$, $R^2$, $R^3$, $l$ and $n$ have the same meaning as defined above.

Some of the compounds represented by the formula (II) are novel and others are known as described in U.S. Pat. Nos. 3,917,609, 3,896,131, 3,985,882, 3,969,463, 4,001,243 and 4,014,877. They can be prepared, for example, by the following Reaction Scheme 1.

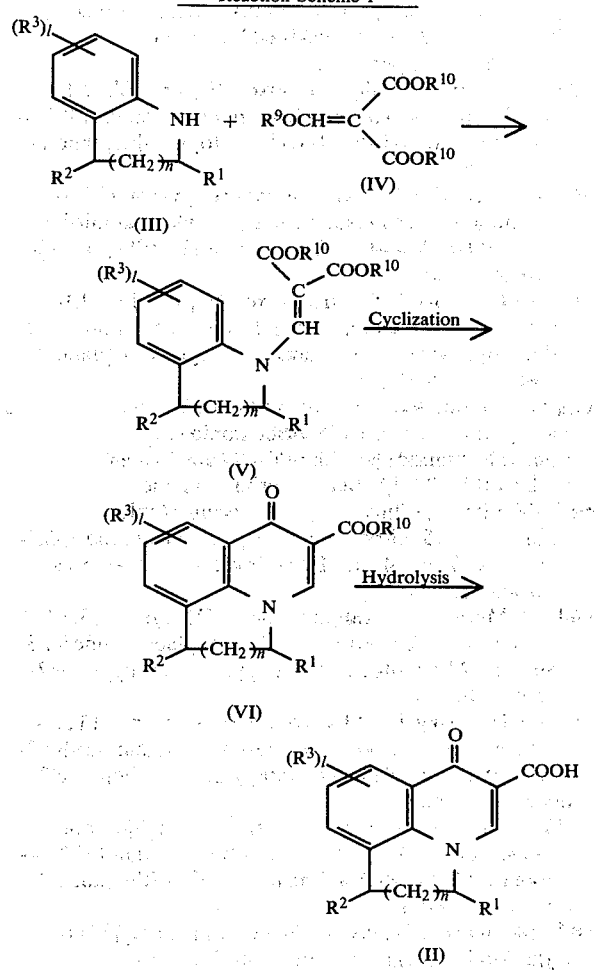

wherein $R^1$, $R^2$, $R^3$, $l$ and $n$ have the same meaning as defined above, and $R^9$ and $R^{10}$ each represents a lower alkyl group.

The compounds of the formula (III) used as starting materials in the above process are known compounds as described in the above U.S. Patents to Gerster et al; Bayer, Annalen, 278, 105 (1894), and Schmidt and Sitwart, Berichte, 45, 1779 (1912), or can be easily prepared in accordance with the known procedures as described in the above U.S. patents and literature references. The compounds of the formula (IV) are known compounds and commercially available. The reaction between the compounds of the formula (III) and the compound of the formula (IV) can be effected in the absence of solvent or in the presence of solvents such as methanol, ethanol, iropropanol, acetonitrile, dimethylformamide, dimethyl sulfoxide, hexamethylphosphoric triamide and the like, preferably in the absence of solvents.

The compound of the formula (IV) can be used in excess, i.e., amounts over the equimolar amount relative to the compounds of the formula (III). Preferably the reaction is carried out in an equimolar amounts in the absence of solvents, or in an amount of from 1.1 to 1.5 mol of the compounds of the formula (IV) per mol of the compound of the formula (III) in the presence of solvents. The reaction can generally be carried out at a temperature of from room temperature (about 15° to 30° C.) to about 150° C., preferably 100° to 130° C., for a period of from about 0.5 to about 6 hours thereby easily yielding the compound represented by the formula (V).

The subsequent cyclization reaction of the compound of the formula (V) can be effected in accordance with a conventional cyclization reaction, for example, by heating the compound of the formula (V) or by cyclization using an acidic substance such as phosphorus oxychloride, phosphorus pentachloride, phosphorus trichloride, thionyl chloride, concentrated sulfuric acid, polyphosphoric acid and the like. When the cyclization is effected by heating, it is preferred to heat the compound of the formula (V) in a solvent such as high boiling point hydrocarbons or high boiling point ethers, for example, tetralin diphenyl ether, diethylene glycol dimethyl ether, etc., at a temperature of about 100° to about 250° C., preferably 150° to 200° C. for a period of about 0.5 to about 6 hours. When the cyclization is effected using an acidic substance, the cyclization can be effected in the presence of the acid substance present in an approximately equimolar amount to a large excess, preferably a 10 to 20 molar excess amount, relative to the amount of the compound of the formula (V) at a temperature of about 100° to about 150° C. for a period of about 0.5 to about 6 hours, whereby the desired compounds of the formula (VI) can be produced advantageously.

In the above Reaction Scheme 1, the hydrolysis of the compound of the formula (VI) into the compound of the formula (II) can be achieved by a conventional hydrolysis procedure in the presence of a typical catalyst, for example, a basic compound such as sodium hydroxide, potassium hydroxide, barium hydroxide and the like, or an inorganic or organic acid such as sulfuric acid, hydrochloric acid, nitric acid, acetic acid, an aromatic sulfonic acid and the like. The hydrolysis can be carried out in a solvent such as water, methanol, ethanol, isopropanol, acetone, methyl ethyl ketone, dioxane, ethylene glycol, acetic acid and the like at a temperature of from room temperature to about 200° C., preferably 50° to 150° C., for a period of about 0.5 to about 6 hours.

The compounds of the formula (IIb) below which are included in the formula (II) can be prepared preferably by reacting the compounds of the formula (IIa) with a piperazine derivative of the formula (VII) as illustrated in Reaction Scheme 2 below.

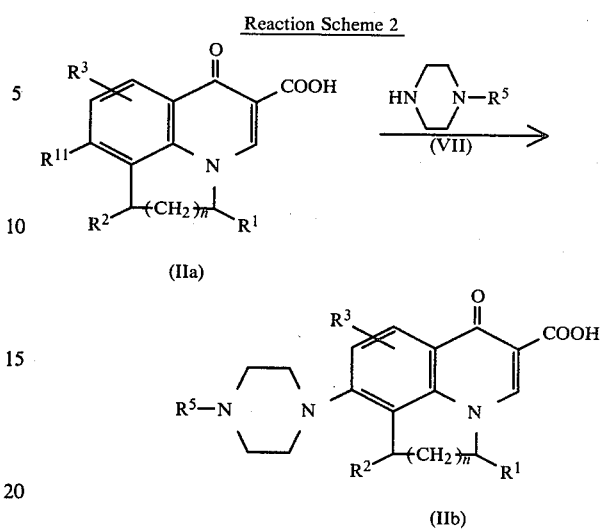

wherein $R^1$, $R^2$, $R^3$, $R^5$ and n have the same meaning as defined above, and $R^{11}$ represents a halogen atom or a lower alkanesulfonyloxy group.

In the reaction of the compound of the formula (IIa) and the compound of the formula (VII), the proportion of the latter to the former is not particularly limited and can be broadly varied. Usually the reaction can be carried out using at least an equimolar amount, preferably 1 to 5 mols, of the compound of the formula (VII) per mol of the compound of the formula (IIa), in an inert solvent.

Suitable examples of the inert solvent include water, lower alcohols such as methanol, ethanol, isopropanol, etc., aromatic hydrocarbons such as benzene, toluene, xylene, etc., ethers such as tetrahydrofuran, dioxane, diglyme (diethylene glycol dimethyl ether), etc., dimethyl sulfoxide, dimethylformamide, hexamethylphosphoric triamide and the like, with dimethyl sulfoxide, dimethylformamide and hexamethylphosphoric triamide being preferred.

The above reaction can be carried out under pressurized conditions, i.e., at a pressure of about 1 to about 20 atms, preferably 1 to 10 atms, at a temperature of about 100° to 250° C., preferably at 140° to 200° C., for a period of about 5 to about 20 hours.

Of the starting compounds of the formula (III), the compounds of the formula (IIIa) and (IIIc) can be prepared with ease in accordance with Reaction Scheme 3 and 4 below.

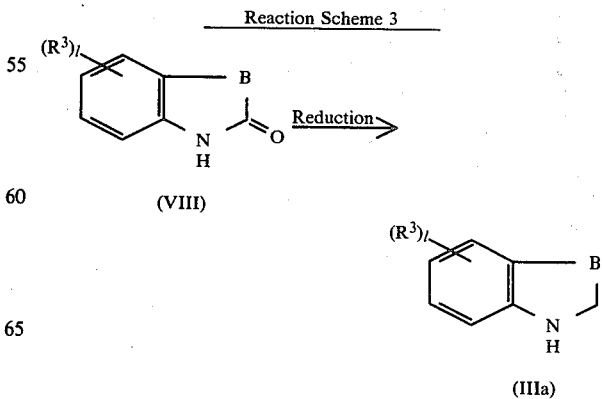

wherein $R^3$ and 1 have the same meaning as defined above, and B represents a methylene group or an ethylene group.

Reaction Scheme 4

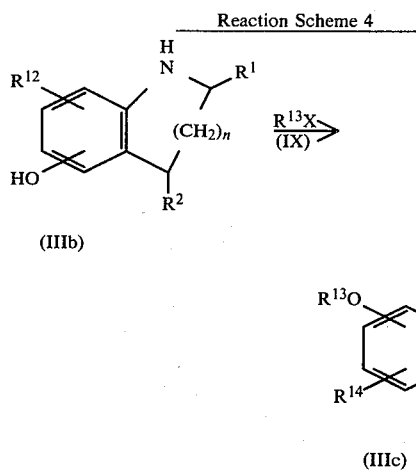

wherein $R^1$, $R^2$ and n have the same meanings as defined above; $R^{12}$ has the same meaning as $R^3$ except for a lower alkenesulfonyloxy group; $R^{13}$ represents a lower alkanesulfonyl group; $R^{14}$ has the same meaning as $R^3$ except for a hydroxy group; and X represents a halogen atom.

In Reaction Scheme 3 above, the reduction of the compounds of the formula (VIII) can be conducted catalytically or using a conventional hydrogenating agent such as a combination of sodium borohydride or lithium aluminium hydride and a lower fatty acid, e.g., acetic acid, trifluoroacetic acid, propionic acid, etc.

Suitable amounts of sodium borohydride or lithium aluminum hydride and the lower fatty acid are an approximately equimolar amount to a large excess amount, preferably 3 to 5 mols per mol of the compound of the formula (VIII), respectively.

The reduction reaction using a hydrogenating agent can proceed advantageously in an inert solvent such as ethers, e.g., dioxane, tetrahydrofuran, diglyme, etc., aromatic hydrocarbons, e.g., benzene, toluene, etc., lower fatty acids, e.g., trifluoroacetic acid, propionic acid, etc., at a temperature of room temperature to about 100° C., preferably 50° to 100° C. for about 1 to about 6 hours.

In Reaction Scheme 4 above, suitable amount of the compound of the formula (IX) to be reacted with the compound of the formula (IIIb) (described in the U.S. patents to Gerster et al and literature references) is at least an approximately equimolar amount, preferably 1 to 2 mols of the compound of the formula (IX) per mol of the compound of the formula (IIIb).

The reaction proceeds usually in an inert solvent in the presence of a deoxidizing agent in an amount of at least an approximately equimolar amount, preferably 1 to 2 mols, of the deoxidizing agent per mol of the compound of the formula (IIIb) at a temperature of about 0° to about 100° C., preferably at room temperature for about 0.5 to about 6 hours.

Examples of suitable deoxidizing agent include alkali metal hydroxides such as sodium hydroxide, potassium hydroxide, etc., inorganic carbonates such as sodium carbonate, potassium carbonate, potassium hydrogen carbonate, sodium hydrogen carbonate, etc., tertiary amines such as pyridine, quinoline, triethylamine, etc.

Examples of suitable inert solvents include lower alcohols such as methanol, ethanol, isopropanol, etc., ethers such as dioxane, tetrahydrofuran, diglyme, etc., aromatic hydrocarbons such as benzene, toluene, etc., dimethyl sulfoxide, dimethylformamide, hexamethylphosphoric triamide, pyridine, etc.

The compounds of the formula (II) thus-obtained can be converted into penicillanic acid derivatives of this invention in various processes which can generally be classified into the following two groups.

(1) The compound of the formula (II) or the carboxyl-activated derivative thereof is reacted with a conventional ampicillin derivative or cephaloglycine derivative, and (2) The compound of the formula (II) or the carboxyl-activated derivative thereof is reacted with a phenylglycine derivative or the amino-activated derivative thereof and the product is further reacted with 6-aminopenicillanic acid derivative or 7-aminocephalosporic acid derivative.

The above processes (1) and (2) can be achieved by conventional amido formation reactions. Representative examples of the processes of group (1) include:

(a) Mixed Acid Anhydride Process

The compound of the formula (II) is reacted with an alkyl haloformate to form mixed acid anhydride thereof which is then reacted with an ampicillin derivative or cephaloglycine derivative.

(b) Activated Ester Process

The compound of the formula (II) is converted into a reactor ester such as a p-nitrophenyl ester, an N-hydroxysuccinimide ester, a 1-hydroxybenzotriazole ester, etc., which is then reacted with an ampicillin derivative or a cephaloglycine derivative.

(c) Carbodiimide Process

The compound of the formula (II) and an ampicillin derivative or a cephaloglycine derivative are condensed while releasing water in the presence of a dehydrating agent such as dicyclohexyldicarboximide, carbonyldiimidazole, etc.

(d) Other Process

The compound of the formula (II) is converted into an acid anhydride using a dehydrating agent such as acetic anhydride, etc., or into acid halide using a halogenating agent followed by reacting the product with an ampicillin derivative or a cephaloglycine derivative; or process in which the lower alcohol ester of the compound of the formula (II) is reacted with an ampicillin derivative or a cephaloglycine derivative at high temperatures under pressurized conditions.

Of the above processes particularly preferred is the mixed acid anhydride process, which can be carried out, for example, in accordance with the following Reaction Scheme 5.

Reaction Scheme 5

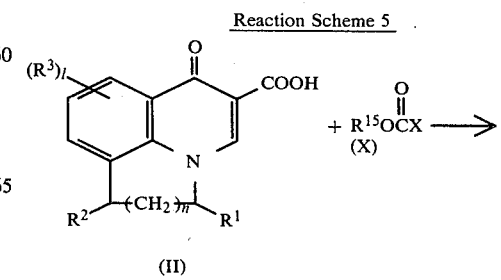

-continued
Reaction Scheme 5

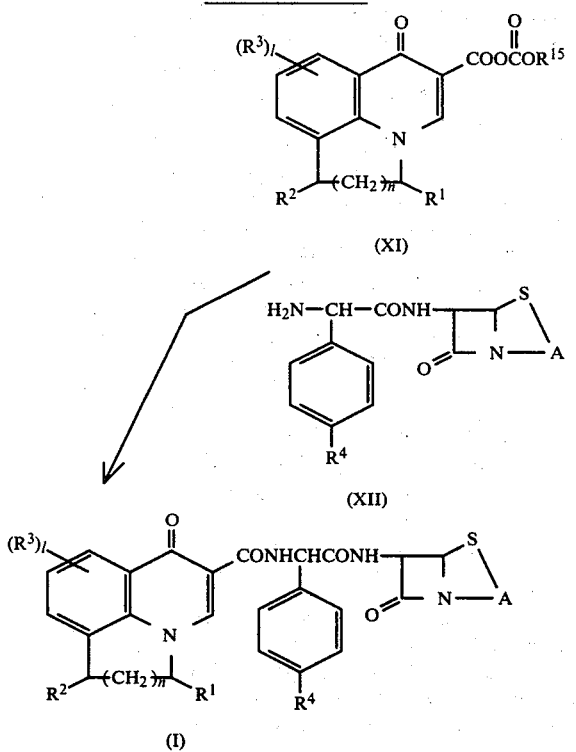

wherein $R^1$, $R^2$, $R^3$, $R^4$, $l$, $n$ and $A$ have the same meaning as defined above, $R^{15}$ represents a lower alkyl group, and X represents a halogen atom.

In Reaction Scheme 5 above, the reaction between the compound of the formula (II) and the alkyl haloformate of the formula (X), which is a known compound, can be achieved in accordance with conventional Schotten-Baumann reaction and the resulting compound of the formula (XI) (a carboxyl-activated derivative of the compound of the formula (II)) can be subjected further to reaction with an ampicillin derivative or cephaloglycine derivative of the formula (XII) without isolation. The ampicillin derivatives and cephaloglycine derivatives of the formula (XII) are described in F. P. Doyle et al, *J. Chem. Soc.*, 1440 (1962) and J. L. Spencer et al, *J. Med. Chem.* 9, 746 (1966).

The Schotten-Baumann reaction applied to the reaction between the compounds of the formula (II) and the compounds of the formula (X) can be effected without solvent in the presence of a basic compound. The reaction proceeds advantageously in a solvent in the presence of a basic compound.

Examples of suitable solvents include chloroform, dichloromethane, dichloroethane, acetonitrile, dimethylformamide, dimethyl sulfoxide, hexamethylphosphoric triamide, etc.

Examples of suitable basic compounds include amines such as triethylamine, trimethylamine, pyridine, dimethylaniline, N-methylmorpholine, etc., metal salts of inorganic acid such as potassium carbonate, sodium carbonate, potassium hydrogen carbonate, sodium hydrogen carbonate, etc., metal salts of organic acids such as sodium acetate, sodium propionate, etc.

Examples of suitable alkyl haloformate include methyl chloroformate, methyl bromoformate, ethyl chloroformate, ethyl bromoformate, isobutyl chloroformate, etc.

The proportion of the compound of the formula (X) to the compound of the formula (II) is generally at least an equimolar amount, and preferably 1.1 to 1.5 mols when the reaction proceeds in a solvent, of the compound of the formula (X) per mol of the compound of the formula (II).

The reaction can be carried out at a temperature of about $-20°$ to about $30°$ C., preferably 0 to room temperature, for about 0.5 to about 3 hours.

The reaction of the compound of the formula (XI) with the compound of the formula (XII) can proceed advantageously in the above-described solvent or a mixture of water and the solvent using at least an approximately equimolar, preferably 1 to 1.5 mols, of the compound of the formula (XII) per mol of the compound (XI) at a temperature of room temperature to about $100°$ C., preferably at room temperature for about 2 to about 10 hours.

A representative example of the group (2) processes is illustrated in the following Reaction Scheme 6.

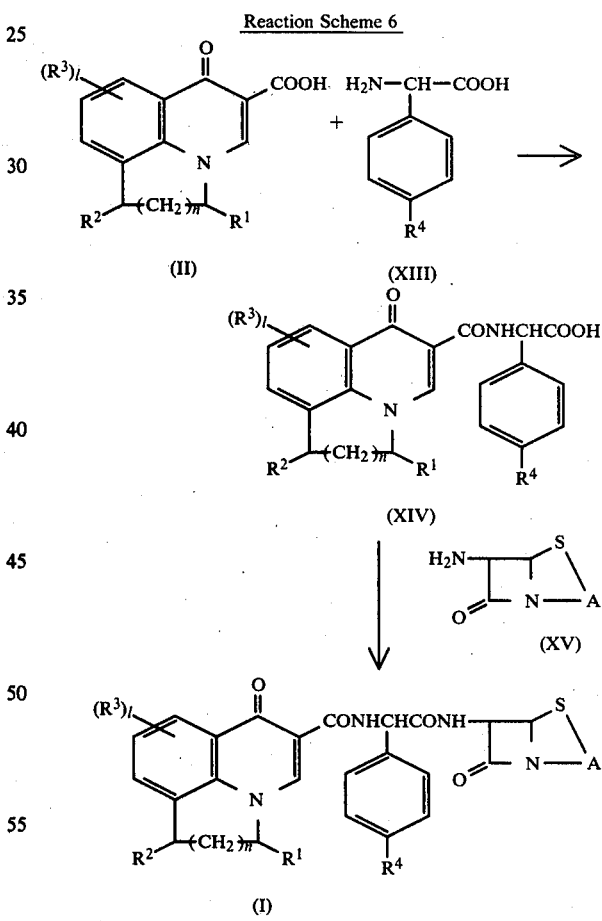

wherein $R^1$, $R^2$, $R^3$, $R^4$, $l$, $n$ and $A$ have the same meaning as defined above.

According to Reaction Scheme 6, the compound of this invention represented by the formula (I) can be obtained by reacting the compound of the formula (II) or the carboxyl-activated derivative thereof with a phenylglycine derivative of the formula (XIII) (a known compound) to form the compound of the formula (XIV) and reacting the compound of the formula (XIV) thus obtained with a 6-aminopenicillanic acid derivative or 7-aminocephalosporic acid derivative or the salts thereof of the formula (XV). The penicillanic acid and cephalosporic acid derivatives and the salts thereof are described in F. P. Doyle et al, *J. Chem. Soc.*, 1440 (1962) and J. L. Spencer et al, *J. Med. Chem.*, 9, 746 (1966).

The reaction steps can be carried out with ease, for example, in accordance with the conventional amido bond formation reaction.

The compounds of this invention represented by the formula (I) prepared as described above can form pharmaceutically acceptable salts with acids when the compound of the formula (I) has a basic group, and this invention also includes within its scope such pharmaceutically acceptable salts. The pharmaceutically acceptable acids which can be used for the salt formation can be various organic or inorganic acids, for example, hydrochloric acid, sulfuric acid, nitric acid, hydrobromic acid, phosphoric acid, acetic acid, oxalic acid, malonic acid, succinic acid, maleic acid, fumaric acid, malic acid, mandelic acid, ethanesulfonic acid, p-toluenesulfonic acid and the like.

The compounds of the formula (I) can be converted into a corresponding carboxylate by reacting the carboxylic acid with a pharmaceutically acceptable basic compound. Examples of basic compounds are inorganic basic compounds such as sodium hydroxide, potassium hydroxide, calcium hydroxide, aluminum hydroxide, sodium bicarbonate and the like and organic basic compounds such as morpholine, piperazine, pyridine, piperidine, ethylamine, dimethylamine, triethylamine, aniline and the like.

The compounds of the formula (I) and the salts thereof obtained as described above can be isolated from the respective reaction mixtures upon completion of the reaction and purified by conventional procedures, for example, solvent extraction, dilution method, precipitation, recrystallization, column chromatography, preparative thin layer chromatography and the like.

As is apparent to those skilled in the art, the compounds of the formula (I) can exist in optically active forms and this invention includes such optical isomers within its scope.

In using the compounds of this invention of the formula (I) and the salts thereof as therapeutic agents, these compounds can be formulated into pharmaceutical compositions together with ordinary pharmaceutically acceptable carriers. Suitable carriers which can be used are, for example, diluents or excipients such as fillers, extenders, binders, wetting agents, disintegrants, surface active agents and lubricants which are usually employed to prepare such drugs depending on the type of dosage form.

Various dosage forms of the therapeutic agents as a antimicrobial agent can be selected according to the purpose of the therapy. Typical dosage forms which can be used are tablets, pills, powders, liquid preparations, suspensions, emulsions, granules, capsules, suppositories, and injectable preparations (solutions, suspensions, etc.).

In molding a pharmaceutical composition containing the compounds of the formula (I) or the pharmaceutically acceptable salt thereof as an active ingredient into a tablet form, a wide range of carriers known in the art can be used. Examples of suitable carriers include excipients such as lactose, white sugar, sodium chloride, glucose solution, urea, starch, calcium carbonate, kaolin, crystalline cellulose and silicic acid, binders such as water, ethanol, propanol, simple syrup, glucose, starch solution, gelatin solution, carboxymethyl cellulose, shellac, methyl cellulose, potassium phosphate and polyvinyl pyrrolidone, disintegrants such as dried starch, sodium alginate, agar powder, laminaria powder, sodium hydrogen carbonate, calcium carbonate, Tween, sodium lauryl sulfate, stearic acid monoglyceride, starch, and lactose, disintegration inhibitors such as white sugar, stearic acid glyceryl ester, cacao butter and hydrogenated oils, absorption promotors such as quaternary ammonium bases and sodium lauryl sulfate, humectants such as glycerol and starch, adsorbents such as starch, lactose, kaolin, bentonite and colloidal silicic acid, and lubricants such as purified talc, stearic acid salts, boric acid powder, Macrogol (trade name for a polyethylene glycol produced by Shinetsu Chemical Industry Co., Ltd.) and solid polyethylene glycol.

The tablets, if desired, can be coated, and made into sugar-coated tablets, gelatin-coated tablets, enteric-coated tablets, film-coated tablets, or tablets comprising two or more layers.

In molding the pharmaceutical composition into pills, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, gelatin, and ethanol, and disintegrants such as laminaria and agar.

In molding the pharmaceutical composition into a suppository form, a wide variety of carriers known in the art can be used. Examples of suitable carriers include polyethylene glycol, cacao butter, higher alcohols, esters of higher alcohols, gelatin, and semi-synthetic glycerides.

When the pharmaceutical composition is formulated into an injectable preparation, the resulting solution and suspension are preferably sterilized, and are isotonic with respect to the blood. In formulating the pharmaceutical composition into the form of a solution or suspension, all diluents customarily used in the art can be used. Examples of suitable diluents are water, ethyl alcohol, propylene glycol, ethoxylated isostearyl alcohol, polyoxyethylene sorbitol, and sorbitan esters. Sodium chloride, glucose or glycerol may be incorporated into a therapeutic agent, e.g., as a nephritis treating agent in an amount sufficient to prepare isotonic solutions. The therapeutic agent may further contain ordinary dissolving aids, buffers, pain-alleviating agents, and preservatives, and optionally coloring agents, perfumes, flavors, sweeteners, and other drugs.

The amount of the compound of the formula (I) and the pharmaceutically acceptable salts thereof of this invention as an active ingredient to be incorporated into a pharmaceutical composition useful as an antimicrobial agent is not particularly limited, and can vary over a wide range. A suitable therapeutically effective amount of the compound of the general formula (I) and the pharmaceutically acceptable salts thereof of this invention is usually about 1 to about 70% by weight, preferably 5 to 50% by weight, based on the entire composition.

There is no particular restriction on the manner of using the therapeutic agent e.g., as a nephritis treating agent, and the therapeutic agent can be administered by routes suitable for the particular forms of the therapeutic agent. For example, the tablets, pills, liquid preparations, suspensions, emulsions, granules, and capsules are orally administered. The injectable preparations are intravenously administered either alone or together with ordinary auxiliary agents such as glucose and amino acids. Furthermore, as required, the therapeutic agent can be singly administered intramuscularly, intracutaneously, subcutaneously, or intraperitoneally. The suppository is administered intrarectally and the ointment is coated on the skin.

The dosage of the antimicrobial agent is suitably selected according to the purpose of use, the symptoms, etc. Usually, a preferred dosage of the compound of this invention is about 10 mg to 5 g/body per day in 3 to 4 multiple doses.

Antimicrobial Activity

1. Test Method

The antimicrobial activity of the following test compounds on various test organisms listed below ($1 \times 10^8$ cells/ml; $OD_{660\ m\mu} = 0.13-0.14$) was determined by the serial dilution method on agar plate and the minimum inhibitory concentrations (mcg/ml) obtained are shown in Table 1 below.

Sample of each test organism was prepared so that the inoculum size of the organism was $1 \times 10^8$ cells/ml ($OD_{660\ m\mu} = 0.13-0.14$).

2. Test Organisms

A: *Staphylococcus aureus* FDA 209 P
B: *Streptococcus pyogenes* IID S-23
C: *Escherichia coli* NIHJ
D: *Klebsiella pneumoniae*
E: *Proteus rettgeri* NIH 96
F: *Salmonella typhi* 0-901 (NCTC 8390)
G: *Shigella sonnei* EW 33
H: *Serratia marcescens* IFO 12648
I: *Pseudomonas aeruginosa* E-2
J: *Pseudomonas aeruginosa* NCTC 10490
K: *Pseudomonas aeruginosa* ATCC 10145
L: *Pseudomonas aeruginosa* NC-5
M: *Pseudomonas aeruginosa* NO. 12

3. Test Compounds

No.1 6-[2-(7a,8,9,10,11,11a-hexahydro-4-oxo-4H-pyrido[3,2,1-jk]carbazole-5-carboxamido)-2-phenylacetamido]-3,3-dimethyl-7-oxo-4-thia-1-azabicyclo[3,2,0]heptane-2-carboxylic acid No.2 6-[2-(6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid No.3 6-[2-(5-methyl-6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid No.4 6-[2-(5-methyl-6,7-dihydro-1-oxo-1H,5H-benzo[ij]quinolizine-2-carboxamido)-2-(4-hydroxy)phenylacetamido]-3,3-dimethyl-7-oxo-4-thia-1-azabicyclo[3,2,0]heptane-2-carboxylic acid No.5 6-{2-[8-(1-piperazinyl)-6,7-dihydro-1-oxo-1H,5H-benzo[ij]quinolizine-2-carboxamido]-2-phenylacetamido}-3,3-dimethyl-7-oxo-4-thia-1-azabicyclo[3,2,0]heptane-2-carboxylic acid No.6 6-{2-[8-(4-acetyl-1-piperazinyl)-6,7-dihydro-1-oxo-1H,5H-benzo[ij]quinolizine-2-carboxamido]-2-phenylacetamido}-3,3-dimethyl-7-oxo-4-thia-1-azabicyclo[3,2,0]heptane-2-carboxylic acid No.7 6-{2-[8-(4-methanesulfonyl-1-piperazinyl)-6,7-dihydro-1-oxo-1H,5H-benzo[ij]quinolizine-2-carboxamido]-2-phenylacetamido}-3,3-dimethyl-7-oxo-4-thia-1-azabicyclo[3,2,0]heptane-2-carboxylic acid No.8 6-{2-[10-chloro-8-(1-piperazinyl)-6,7-dihydro-1-oxo-1H,5H-benzo[ij]quinolizine-2-carboxamido]-2-phenylacetamido}-3,3-dimethyl-7-oxo-4-thia-1-azabicyclo[3,2,0]heptane-2-carboxylic acid No.9 6-[2-(2-fluoro-7a,8,9,10,11,11a-hexahydro-4-oxo-4H-pyrido[3,2,1-jk]carbazole-5-carboxamido)-2-phenylacetamido]-3,3-dimethyl-7-oxo-4-thia-1-azabicyclo[3,2,0]heptane-2-carboxylic acid No.10 6-[2-(2-methoxy-7a-8,9,10,11,11a-hexahydro-4-oxo-4H-pyrido[3,2,1-jk]carbazole-5-carboxamido)-2-phenylacetamido]-3,3-dimethyl-7-oxo-4-thia-1-azabicyclo[3,2,0]heptane-2-carboxylic acid No.11 6-[2-(1,3-dimethyl-7a,8,9,10,11,11a-hexahydro-4-oxo-4H-pyrido[3,2,1-jk]carbazole-5-carboxamido)-2-phenylacetamido]-3,3-dimethyl-7-oxo-4-thia-1-azabicyclo[3,2,0]heptane-2-carboxylic acid No.12 6-[2-(3-nitro-7a,8,9,10,11,11a-hexahydro-4-oxo-4H-pyrido[3,2,1-jk]carbazole-5-carboxamido)-2-phenylacetamido]-3,3-dimethyl-7-oxo-4-thia-1-azabicyclo[3,2,0]heptane-2-carboxylic acid No.13 6-[2-(3-acetylamino-7a,8,9,10,11,11a-hexahydro-4-oxo-4H-pyrido[3,2,1-jk]carbazole-5-carboxamido)-2-phenylacetamido]-3,3-dimethyl-7-oxo-4-thia-1-azabicyclo[3,2,0]heptane-2-carboxylic acid No.14 6-[2-(2-hydroxy-7a,8,9,10,11,11a-hexahydro-4-oxo-4H-pyrido[3,2,1-jk]carbazole-5-carboxamido)-2-phenylacetamido]-3,3-dimethyl-7-oxo-4-thia-1-azabicyclo[3,2,0]heptane-2-carboxylic acid No.15 6-[2-(7a,8,9,10,11,11a-hexahydro-4-oxo-4H-pyrido[3,2,1-jk]carbazole-5-carboxamido)-2-(4-hydroxy)phenylacetamido]-3,3-dimethyl-7-oxo-4-thia-1-azabicyclo[3,2,0]heptane-2-carboxylic acid No.16 6-[2-(9-fluoro-6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid No.17 6-[2-(10-amino-6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid No.18 6-[2-(9-methyl-6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid No.19 6-[2-(9-hydroxy-6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid No.20 6-[2-(6,7-dihydro-1-oxo-1H,5H-benzo[ij]quinolizine-2-carboxamido)-2-(4-hydroxy)-phenylacetamido]-3,3-dimethyl-7-oxo-4-thia-1-azabicyclo[3,2,0]heptane-2-carboxylic acid No.21 6-{2-[8-(4-formyl-1-piperazinyl)-6,7-dihydro-1-oxo-1H,5H-benzo[ij]quinolizine-2-carboxamido]-2-(4-hydroxy)phenylacetamido}-3,3-dimethyl-7-oxo-4-thia-1-azabicyclo[3,2,0]heptane-2-carboxylic acid No.22 6-[2-(1,2-dihydro-6-oxo-6H-pyrrolo[3,2,1-ij]quinoline-5-carboxamido)-2-phenylacetamido]-3,3-dimethyl-7-oxo-4-thia-1-azabicyclo[3,2,0]heptane-2-carboxylic acid No.23 7-[2-(6,7-dihydro-1-oxo-1H,5H-benzo[ij]quinolizine-2-carboxamido)-2-phenylacetamido]-3-(acetyloxymethyl)-8-oxo-5-thia-1-azabicyclo[4,2,0]oct-2-ene-2-carboxylic acid No.24 7-[2-(5-methyl-6,7-dihydro-1-oxo-1H,5H-benzo[ij]quinolizine-2-carboxamido)-2-phenylacetamido]-3-[5-(1-methyl-1,2,3,4-tetrazole)- thiomethyl]-8-oxo-5-thia-1-azabicyclo[4,2,0]oct-2-ene-2-carboxylic acid dicyclohexylamine
No.25 carbenicillin (control)
No.26 ampicillin
No.27 cephaloglycine
No.28 9-fluoro-5-methyl-6,7-dihydro-1-oxo-1H,5H-benzo[ij]quinolizine-2-carboxylic acid
No.29 sodium 9-chloro-2-methyl-6-oxo-1,2-dihydro-6H-pyrrolo[3,2,1-ij]quinoline-5-carboxylate

TABLE 1

| Test Compound No. | Minimum Inhibitory Concentration (μg/ml) Test Organisms |||||||||||||
|---|---|---|---|---|---|---|---|---|---|---|---|---|
| | A | B | C | D | E | F | G | H | I | J | K | L | M |
| 1 | <0.1 | 3.1 | 6.3 | — | — | 0.8 | — | 6.3 | — | — | 3.1 | 0.4 | 1.6 |
| 2 | 0.8 | 0.8 | 3.1 | 6.3 | 3.1 | 1.6 | 3.1 | 25 | — | — | 6.3 | 25 | 12.5 |
| 3 | 0.4 | 12.5 | 6.3 | 3.1 | 6.3 | 3.1 | 3.1 | 12.5 | 12.5 | 1.6 | 12.5 | 0.8 | 12.5 |
| 4 | 0.8 | 12.5 | 6.3 | 6.3 | 12.5 | 3.1 | 3.1 | 50 | 25 | 1.6 | 12.5 | 1.6 | 25 |
| 5 | 0.1 | — | 1.6 | 0.8 | 0.4 | 0.2 | 3.1 | 12.5 | 25 | 6.3 | 25 | 6.3 | 50 |
| 6 | 1.6 | — | 6.3 | 12.5 | 25 | 6.3 | 12.5 | 50 | 25 | 3.1 | 12.5 | 1.6 | 25 |
| 7 | 0.8 | — | 3.1 | 6.3 | 12.5 | 3.1 | 6.3 | 50 | 25 | 3.1 | 12.5 | 3.1 | 50 |
| 8 | 0.8 | — | 6.3 | 6.3 | 12.5 | 3.1 | 3.1 | 25 | 25 | 3.1 | 12.5 | 6.3 | 25 |
| 9 | 0.8 | — | 12.5 | 6.3 | 6.3 | 3.1 | 3.1 | 12.5 | 12.5 | 1.6 | 12.5 | 1.6 | 12.5 |
| 10 | 1.6 | — | 12.5 | 6.3 | 12.5 | 6.3 | 6.3 | 12.5 | 12.5 | 3.1 | 25 | 3.1 | 25 |
| 11 | 1.6 | — | 12.5 | 12.5 | 12.5 | 3.1 | 3.1 | 12.5 | 25 | 6.3 | 25 | 6.3 | 12.5 |
| 12 | 1.6 | — | 6.3 | 6.3 | 3.1 | 1.6 | 3.1 | 6.3 | 12.5 | 1.6 | 6.3 | 1.6 | 12.5 |
| 13 | 1.6 | — | 6.3 | 3.1 | 3.1 | 1.6 | 3.1 | 12.5 | 12.5 | 6.3 | 6.3 | 3.1 | 12.5 |
| 14 | 1.6 | — | 6.3 | 6.3 | 6.3 | 6.3 | 6.3 | 12.5 | 25 | 6.3 | 6.3 | 3.1 | 12.5 |
| 15 | 0.2 | — | 6.3 | 3.1 | 6.3 | 3.1 | 3.1 | 12.5 | 12.5 | 1.6 | 12.5 | 1.6 | 12.5 |
| 16 | 0.8 | — | 6.3 | 3.1 | 6.3 | 3.1 | 3.1 | 12.5 | 12.5 | 3.1 | 12.5 | 3.1 | 12.5 |
| 17 | 1.6 | — | 12.5 | 6.3 | 6.3 | 6.3 | 6.3 | 25 | 25 | 6.3 | 25 | 6.3 | 25 |
| 18 | 0.8 | — | 3.1 | 1.6 | 3.1 | 1.6 | 1.6 | 6.3 | 25 | 3.1 | 12.5 | 3.1 | 12.5 |
| 19 | 0.8 | — | 6.3 | 3.1 | 3.1 | 3.1 | 3.1 | 6.3 | 12.5 | 3.1 | 12.5 | 1.6 | 12.5 |
| 20 | 0.8 | — | 3.1 | 3.1 | 6.3 | 3.1 | 3.1 | 12.5 | 12.5 | 3.1 | 12.5 | 3.1 | 12.5 |
| 21 | 1.6 | — | 3.1 | 12.5 | 12.5 | 3.1 | 3.1 | 100 | 12.5 | 3.1 | 3.1 | 3.1 | 50 |
| 22 | 0.4 | — | 1.6 | 3.1 | 6.3 | 3.1 | 3.1 | 12.5 | 12.5 | 3.1 | 12.5 | 3.1 | 12.5 |
| 23 | 12.5 | — | 3.1 | 6.3 | 6.3 | 6.3 | 50 | 50 | 50 | 12.5 | 12.5 | 12.5 | 50 |
| 24 | 6.3 | — | 1.6 | 6.3 | 3.1 | 3.1 | 25 | 25 | 25 | 6.3 | 6.3 | 6.3 | 25 |
| 25 | 1.6 | >100 | 12.5 | 6.3 | 0.4 | 3.1 | 1.6 | 12.5 | 100 | 1.6 | 100 | 12.5 | >100 |
| 26 | 0.05 | — | 3.1 | 1.6 | 6.3 | 0.8 | 1.6 | — | >100 | >100 | >100 | >100 | >100 |
| 27 | 1.6 | — | 3.1 | 1.6 | — | 1.6 | 6.3 | 50 | >100 | >100 | >100 | >100 | >100 |
| 28 | 3.1 | >100 | 0.2 | 0.8 | 0.2 | 0.2 | 0.8 | 0.8 | 50 | 25 | 25 | — | — |
| 29 | 3.1 | >100 | 0.8 | 3.1 | 0.4 | 0.8 | 1.6 | 3.1 | 100 | 25 | 50 | — | — |

Acute Toxicity

The acute toxicity of the compounds of this invention was determined by intravenous administration (i.v.) in mice which had been fasted for 12 hours prior to the test. $LD_{50}$ values (50% lethal dose) obtained are shown in Table 2 below.

TABLE 2

| Test Compound No. | Acute Toxicity $L_{50}$ (i.v.) (mg/kg) |
|---|---|
| 1 | 1,000–1,100 |
| 2 | 1,000 |
| 3 | 1,000–1,100 |

In the same manner as above were obtained $LD_{50}$ values of the other test compounds which amounted to 500 mg/kg or more.

The present invention is further illustrated by the following Reference Examples (preparation of starting materials) and Examples, but they are not to be construed as limiting the scope of this invention. The antimicrobial activity of typical compounds of the present invention are also shown in the Examples. Unless otherwise indicated, all parts, percents and ratios are by weight.

REFERENCE EXAMPLE 1

12.6 g of p-fluoroaniline was dissolved in 100 ml of ethanol and a catalytic amount of p-toluenesulfonic acid was added thereto. 9.8 g of cyclohexanone was then added dropwise to the mixture at room temperature. After completion of the addition, the mixture was stirred at room temperature for 1 hour and concentrated under reduced pressure. Dilute sulfuric acid prepared from 190 ml of water and 20 ml of concentrated sulfuric acid was added to the residue and the mixture was heated at 110° C. for 15 minutes on an oil bath to precipitate light orange crystals. The crystals thus formed were filtered, washed 3 times with water and dried to obtain 17.4 g of 6-fluoro-1,2,3,4-tetrahydrocarbazole which was identified by NMR spectrum.

REFERENCE EXAMPLE 2

10 g of 6-fluoro-1,2,3,4-tetrahydrocarbazole was dissolved in 75 ml of glacial acetic acid and 15 g of tin metal was added to the solution. The mixture was heated on an oil bath while refluxing and then 50 ml of concentrated hydrochloric acid was added dropwise thereto. The color of the reaction system changed from orange color to colorless with vigorous genaration of hydrogen. After reaction for 3.5 hours, any excess of tin metal was removed by filtration, and the filtrate was concentrated. 50 ml of water was added to the residue, and the mixture was rendered alkaline with 4 N sodium hydroxide and extracted with diethyl ether. The ether layer was dried over anhydrous sodium sulfate, filtered and concentrated to obtain 10 g of 6-fluoro-1,2,3,4,10,11-hexahydrocarbazole as white crystals having a melting point of 80°–83° C. The production of the above compound was confirmed by NMR spectrum.

REFERENCE EXAMPLE 3

9 g of ethyl ethoxymethylenemalonate was added to 8 g of 6-fluoro-1,2,3,4,10,11-hexahydrocarbazole and the mixture was heated at 110° C. on an oil bath during which time distillation of ethanol was observed. After heating the mixture at the same temperature as above for 30 minutes, 100 g of polyphosphoric acid was added thereto followed by heating at 140° C. for 30 minutes. After completion of the reaction, the reaction mixture was poured into 500 ml of water to obtain light brown crystals which were then recrystallized from a mixture of benzene-hexane (1:1) to obtain 14 g of ethyl 2-fluoro-7a,8,9,10,11,11a-hexahydro-4-oxo-4H-pyrido[3,2,1-jk]carbazole-5-carboxylate as white plates having a melting point of 97°-98° C.

REFERENCE EXAMPLE 4

21.6 g of ethyl ethoxymethylenemalonate was added to 17.5 g of 1,2,3,4,10,11-hexahydrocarbazole and the mixture was heated at 110° C. on an oil bath for 30 minutes while stirring, during which time distillation of ethanol was observed. After heating, 240 g of polyphosphoric acid prepared from 120 g of phosphoric acid and 120 g of phosphoric pentoxide was added to the mixture and the mixture was allowed to react on an oil bath at 140° C. for 45 minutes. After completion of the reaction, the mixture was allowed to cool to room temperature and poured into 400 ml of water, followed by rendering the mixture neutral with 40% aqueous sodium hydroxide to precipitate light purple crystals. The crystals thus-obtained were recrystallized from benzene-hexane (1:1) to obtain 32 g of ethyl 7a,8,9,10,11,11a-hexahydro-4-oxo-4H-pyrido[3,2,1-jk]carbazole-5-carboxylate having a melting point of 71°-73° C.

REFERENCE EXAMPLE 5

8.36 g (0.0387 mol) of ethyl ethoxymethylenemalonate was added to 7.32 g (0.0387 mol) of 6-methyl-1,2,3,4,10,11-hexahydrocarbazole and the mixture was heated on an oil bath at 110° C., during which time distillation of ethanol was observed. After heating the mixture at the same temperature as above, 100 g of polyphosphoric acid was added thereto followed by heating at 140° C. for 40 minutes. After completion of the reaction, the reaction mixture was poured into 200 ml of water and the resulting mixture was rendered neutral with 20% aqueous sodium hydroxide while cooling to precipitate light brown crystals which were recrystallized from benzenehexane (1:1) to obtain 12 g of ethyl 2-methyl-7a,8,9,10,11,11a-hexahydro-4-oxo-4H-pyrido[3,2,1-jk]carbazole-5-carboxylate as colorless plates having a melting point of 107°-109° C.

REFERENCE EXAMPLE 6

140 ml of a 10% aqueous sodium hydroxide solution was added to 10 g of ethyl 2-fluoro-7a,8,9,10,11,11a-hexahydro-4-oxo-4H-pyrido[3,2,1-jk]carbazole-5-carboxylate, followed by heat-refluxing for 40 minutes. The crystals of the above starting material were dissolved to give a uniform solution. The solution was treated with activated carbon while hot, and filtered. The filtrate was cooled, and adjusted to pH 2 with concentrated hydrochloric acid to obtain 8 g of white crystals. The resulting crystals were recrystallized from ethanol to give 2-fluoro-7a,8,9,10,11,11a-hexahydro-4-oxo-4H-pyrido[3,2,1-jk]carbazole-5-carboxylic acid as white needles having a melting point of 281°-282° C.

REFERENCE EXAMPLE 7

250 ml of a 10% aqueous sodium hydroxide solution was added to 28 g of ethyl 7a,8,9,10,11,11a-hexahydro-4-oxo-4H-pyrido[3,2,1-jk]carbazole-5-carboxylate, followed by heat-refluxing for 2 hours. The reaction system changed from a suspension to a uniform solution as the reaction proceeded. 200 ml of water was added to the reaction mixture which was then filtered, and the filtrate was rendered acidic with concentrated hydrochloric acid to precipitate light yellow crystals. The crystals were separated by filtration, washed successively with water and a small amount of ethanol, dried and recrystallized from chloroform-hexane (1:1 by volume) to obtain 16 g of 7a,8,9,10,11,11a-hexahydro-4-oxo-4H-pyrido[3,2,1-jk]carbazole-5-carboxylic acid as light yellow amorphous crystals having a melting point of 238°-241° C.

REFERENCE EXAMPLE 8

70 ml of a 10% aqueous sodium hydroxide solution was added to 4 g of ethyl 2-methyl-7a,8,9,10,11,11a-hexahydro-4-oxo-4H-pyrido[3,2,1-jk]carbazole-5-carboxylate. The mixture was heat-refluxed for 1.5 hours, allowed to cool to room temperature and filtered. The filtrate was cooled and adjusted to a pH of 2 with concentrated hydrochloric acid to obtain 3.2 g of light yellow crystals. Recrystallization from ethanol gave 2-methyl-7a,8,9,10,11,11a-hexahydro-4-oxo-4H-pyrido[3,2,1-jk]carbazole-5-carboxylic acid as needle crystals having a melting point of 188°-190° C.

REFERENCE EXAMPLES 9 to 13

In the same manner as described in Reference Example 8, the following compounds having the substituents shown in Table 3 below were prepared. The melting point and the crystal form of the resulting products are also shown in Table 3.

TABLE 3

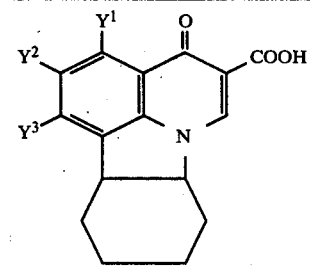

| Reference Example Nos. | $Y_1$ | $Y_2$ | $Y_3$ | Melting Point | Crystal Form (Recrystallization Solvent) |
|---|---|---|---|---|---|
| 9 | H | OCH$_3$ | H | 198-200 | Light Yellow Amorphous (Chloroform-Hexane) |
| 10 | H | Cl | H | 219-221 | Light Yellow Amorphous (Chloroform-Hexane) |
| 11 | CH$_3$ | H | CH$_3$ | 216-217 | Light Brown Needles (Ethanol) |
| 12 | F | H | H | 215-217 | Light Yellow Plates (Ethanol) |
| 13 | NO$_2$ | H | H | 251-253 | Light Yellow Amorphous |

TABLE 3-continued

[Structure: Y¹, Y², Y³ substituted pyrido-carbazole with COOH group]

| Reference Example Nos. | $Y_1$ | $Y_2$ | $Y_3$ | Melting Point | Crystal Form (Recrystallization Solvent) |
|---|---|---|---|---|---|
| | | | | | (DMF-H$_2$O) |

REFERENCE EXAMPLE 14

6 g of 3-nitro-7a,8,9,10,11,11a-hexahydro-4-oxo-4H-pyrido[3,2,1-jk]carbazole-5-carboxylic acid was dissolved in 100 ml of a 2% aqueous potassium hydroxide solution and the solution was catalytically reduced for 3 hours by the Parr method (3 kg/cm²) in the presence of 5 g of Raney nickel. After completion of the reduction, the mixture was filtered and the filter cake on the filter paper was washed with water and the combined filtrate and the washing was rendered neutral with glacial acetic acid to precipitate brown crystals. The resulting crystals were filtered, washed with water, dried and recrystallized from DMF-H$_2$O to obtain 3.7 g of 3-amino-2a,8,9,10,11,11a-hexahydro-4-oxo-4H-pyrido[3,2,1-jk]carbazole-5-carboxylic acid having a melting point of 253°–256° C. (with decomposition).

REFERENCE EXAMPLE 15

2.84 g of 3-amino-7a,8,9,10,11,11a-hexahydro-4-oxo-4H-pyrido[3,2,1-jk]carbazole-5-carboxylic acid was dissolved in 50 ml of a 2% aqueous potassium hydroxide, and acetic anhydride was added dropwise thereto while ice cooling whereby orange-colored crystals were precipitated. The resulting crystals were separated by filtration, washed with water and recrystallized from dimethylformamide-water to obtain 3 g of 3-acetylamino-7a,8,9,10,11,11a-hexahydro-4-oxo-4H-pyrido[3,2,1-jk]carbazole-5-carboxylic acid having a melting point of 187°–190° C.

REFERENCE EXAMPLE 16

6 g of 7a,8,9,10,11,11a-hexahydro-4-oxo-4H-pyrido[3,2,1-jk]carbazole-5-carboxylic acid was dissolved in 35 ml of concentrated sulfuric acid and stirred while cooling with ice, followed by dropwise addition of a mixture of 4.3 ml of concentrated nitric acid having a specific gravity of 1.42 and 15 ml of the concentrated sulfuric acid. After completion of the addition, the resulting mixture was stirred for 1 hour at room temperature and poured into 200 g of ice to precipitate yellow crystals. Recrystallization from dimethylformamide-water gave 7 g of 3-nitro-7a,8,9,10,11,11a-hexahydro-4-oxo-4H-pyrido[3,2,1-jk]carbazole-5-carboxylic acid having a melting point of 251°–253° C.

REFERENCE EXAMPLE 17

9 g of diethyl ethoxymethylenemalonate was added to 9 g of 5-chloro-1,2,3,4-tetrahydrocarbazole and the mixture was heated without solvent at 110° C. on an oil bath for 30 minutes while stirring; during which time distillation of ethanol was observed. After heating, 100 g of polyphosphoric acid prepared from 50 g of phosphoric acid and 50 g of phosphorous pentoxide was added to the mixture and the mixture was allowed to react on an oil bath at 140° C. for 40 minutes. After completion of the reaction, the mixture was allowed to cool to 60° C. and poured into 500 ml of ice water to precipitate light yellow crystals. The crystals thus-formed were filtered and washed with water sufficiently followed by refluxing with 100 ml of a 10% aqueous NaOH solution for 1 hour. The crystals were dissolved to give a uniform solution which was then treated with activated carbon while hot and the pH of the solution was adjusted to 2 with concentrated hydrochloric acid to obtain 9.3 g of 1-chloro-7a,8,9,10,11,11a-hexahydro-4H-pyrido[3,2,1-jk]carbazole-4-oxo-5-carboxylic acid as light yellow crystals having a melting point of 273° to 275° C.

REFERENCE EXAMPLE 18

3.1 g of 1-chloro-7a,8,9,10,11,11a-hexahydro-4H-pyrido[3,2,1-jk]carbazole-4-oxo-5-carboxylic acid was mixed with 5 g of anhydrous piperazine and 50 ml of dimethyl sulfoxide and the mixture was heated at 140° to 150° C. on an oil bath for 4 hours with stirring. After the completion of the reaction, the solvent was removed under reduced pressure. 200 ml of water and 200 ml of chloroform were added to the residue and after shaking the water layer was separated. After adjusting the pH value thereof to a pH of 3, the water layer was filtered. The filtrate was treated with activated carbon and concentrated to obtain light yellow precipitates. The precipitates were washed with a small amount of water and dried to give 1.3 g of 1-(1-piperazinyl)-7a,8,9,10,11,11a-hexahydro-4H-pyrido[3,2,1-jk]carbazole-4-oxo-5-carboxylic acid hydrochloride having a melting point of 289° to 294° C. (decomposition).

REFERENCE EXAMPLE 19

10 g of 5-hydroxy-3,4-dihydrocarbostyril was added to 100 ml of methanol having dissolved therein 3.8 g of potassium hydroxide and the mixture was stirred at room temperature for 30 minutes followed by removing methanol under reduced pressure. Benzene was added to the residue to form crystals and then benzene was removed by evaporation. The residue thus-obtained was suspended in 50 ml of dimethylformamide and 10.6 g of methanesulfonyl chloride was added dropwise to the suspension while ice-cooling with stirring. After adding 3.5 g of methanesulfonyl chloride, the resulting mixture was stirred at room temperature for 4 hours. After the completion of the reaction, the solvent was removed under reduced pressure and the residue was purified through a silica gel column chromatography (silica gel:Wako C-200, a trade name for a product of Wako Junyaku Co., Ltd.; eluant:chloroform). Recrystallization of the eluate from water-containing ethanol gave 5.7 g of 5-methanesulfonyloxy-3,4-dihydrocarbostyril as colorless prismatic crystals having a melting point of 227° to 231° C.

REFERENCE EXAMPLE 20

4.5 g of 5-methanesulfonyloxy-3,4-dihydrocarbostyril was suspended in 90 ml of dioxane and 35 g of NaBH$_4$ was added to the suspension, then 5.3 ml of acetic acid was added dropwise to the mixture. After heat-refluxing the resulting mixture for 1 hour, the solvent was removed under reduced pressure. Saturated aqueous solution of sodium bicarbonate was added to the residue to form precipitates which were filtered and washed with chloroform. The filtrate was extracted with chloroform and the chloroform layer was dried over $Na_4SO_4$ followed by removing the solvent. The residue was purified through a silica gel column chromatography (silica gel:Wako 200, a trade name for a product of Wako Junyaku Co., Ltdl; eluant:chloroform) and the eluate thus-obtained was crystallized from petroleum ether. Recrystallization of the crystals thus-obtained from methanol gave 1.9 g of 5-methanesulfonyloxy-1,2,3,4-tetrahydroquinoline as colorless prisms having a melting point of 74° to 76° C.

REFERENCE EXAMPLE 21

9.5 g of ethyl ethoxymethylenemalonate was added to 5.8 g of 1,2,3,4-tetrahydroquinoline and the mixture was heated on an oil bath at 110° C. during which time distillation of ethanol was observed. After heating the mixture at the same temperature as above for 30 minutes, 60 g of polyphosphoric acid was added thereto followed by heating at 140° C. for 30 minutes. After completion of the reaction, the reaction mixture was poured into 200 ml of water and the resulting mixture was rendered neutral with a 40% aqueous sodium hydroxide solution to precipitate light yellow crystals. The crystals were mixed with 100 ml of a 10% sodium hydroxide solution without further purification and the mixture was heat-refluxed for 40 minutes during which time the crystals were dissolved to form a uniform solution. The solution was treated with activated carbon while hot and filtered. The filtrate was allowed to cool and adjusted to a pH of 2 to obtain 6 g of white crystals. Recrystallization of the crystals from dimethylformamide-water gave 6,7-dihydro-1-oxo-1H,5H-benzo[ij]quinolizine-2-carboxylic acid as white needles having a melting point of 256° to 258° C.

REFERENCE EXAMPLE 22

4.9 g of ethyl ethoxymethylenemalonate was added to 4 g of 6-chloro-1,2,3,4-tetrahydroquinoline and the mixture was heated on an oil bath at 110° C. during which time distillation of ethanol was observed. After heating the mixture at the same temperature as above for 30 minutes, 30 g of polyphosphoric acid was added thereto followed by heating at 140° C. for 30 minutes. After completion of the reaction, the reaction mixture was poured into 200 ml of water and the resulting mixture was rendered neutral with a 40% aqueous sodium hydroxide solution to precipitate light brown crystals. Without further purification, the crystals were mixed with 100 ml of a 10% aqueous sodium hydroxide solution and the mixture was heat-refluxed for 40 minutes during which time the crystals were dissolved to form a uniform solution. The solution was treated with activated carbon while hot and filtered. The filtrate was allowed to cool and adjusted pH value to pH 2 to obtain 7.0 g of 9-chloro-6,7-dihydro-1-oxo-1H,5H-benzo[ij]quinolizine-2-carboxylic acid as light yellow crystals having a melting point of 282° to 286° C.

REFERENCE EXAMPLE 23

3.1 g of ethyl ethoxymethylenemalonate was added to 2.7 g of 5,7-dichloro-1,2,3,4-tetrahydroquinoline and the mixture was heated on an oil bath at 110° C. during which time distillation of ethanol was observed. After heating the mixture at the same temperature as above for 30 minutes, 30 g of polyphosphoric acid was added thereto followed by heating at 140° C. for 30 minutes. After completion of the reaction, the reaction mixture was poured into 100 ml of water and the resulting mixture was rendered neutral with a 40% aqueous sodium hydroxide solution to precipitate light brown crystals. Without further purification the crystals were mixed with 100 ml of a 10% aqueous sodium hydroxide solution and the mixture was heat-refluxed for 40 minutes during which time the crystals were dissolved to form a uniform solution. The solution was treated with activated carbon while hot and filtered. The filtrate was allowed to cool and adjusted to a pH of 2 to obtain 2.7 g of 8,10-dichloro-6,7-dihydro-1-oxo-1H,5H-benzo[ij]quinolizine-2-carboxylic acid as light yellow crystals having a melting point of 300° to 304° C.

REFERENCE EXAMPLE 24

21.6 g of ethyl ethoxymethylenemalonate was added to 22.4 g of 5-methanesulfonyloxy-1,2,3,4-tetrahydroquinoline and the mixture was heated at 110° C. on an oil bath for 30 minutes while stirring, during which time distillation of ethanol was observed. After heating, 240 g of polyphosphoric acid prepared from 120 g of phosphoric acid and 120 g of phosphorus pentoxide was added to the mixture and the mixture was allowed to react on an oil bath at 140° C. for 45 minutes. After completion of the reaction, the mixture was allowed to cool to room temperature and poured into 400 ml of water, followed by rendering the mixture neutral with 40% aqueous sodium hydroxide to precipitate crystals. The crystals thus-obtained were mixed with 150 ml of a 10% aqueous sodium hydroxide solution and the mixture was heat-refluxed for 40 minutes during which time the crystals were dissolved to form a uniform solution. The solution was treated with activated carbon while hot and filtered. The filtrate was allowed to cool and adjusted to a pH of 2 to precipitate crystals which were filtered. Recrystallization of the crude crystals thus-obtained from dimethylformamide gave 21.3 g of 8-methanesulfonyloxy-6,7-dihydro-1-oxo-1H,5H-benzo[ij]quinolizine-2-carboxylic acid as white needles having a melting point of 270° to 275° C.

REFERENCE EXAMPLE 25

19.2 g of 8-chloro-6,7-dihydro-1-oxo-1H,5H-benzo[ij]quinolizine-2-carboxylic acid and 35.5 g of piperazine were added to 350 ml of anhydrous dimethyl sulfoxide and the mixture was heated on an oil bath at 170° to 180° C. for 6 hours while stirring. After completion of the reaction, the solvent was removed under reduced pressure. 500 ml of water was added to the residue and the pH value of the mixture was adjusted to a pH of 2 followed by filtering water-insoluble materials. The filtrate was concentrated to 100 ml under reduced pressure and rendered alkaline (pH=9) with a 10% aqueous sodium hydroxide solution. After extracting the aqueous alkali solution with chloroform to thereby remove chloroform-soluble materials, the aqueous alkali solution layer was allowed to stand to precipitate crystals which were filtered. The crude crystals thus-obtained were dissolved in 10 ml of a 10% aqueous sodium hydroxide solution and the solution was treated with activated carbon and adjusted to a pH of 8 with a 10% aqueous hydrochloric acid solution to precipitate crystals which were filtered and washed with water sufficiently. Recrystallization of the crystals from dimethylformamide gave 6.5 g of 8-(1-piperazinyl)-6,7-dihydro- 1-oxo-1H,5H-benzo[ij]quinolizine-2-carboxylic acid as white needles having a melting point of 267° to 268° C. 6.4 g of 8-(1-piperazinyl)-6,7-dihydro-1-oxo-1H,5H-benzo[ij]quinolizine-2-carboxylic acid thus-obtained was suspended in 50 ml of water and 15 ml of a 10% aqueous hydrochloric acid solution was added to the resulting solution. After removing the insoluble materials by filtration, the water was distilled off to obtain 5.7 g of 8-(1-piperazinyl)-6,7-dihydro-1-oxo-1H,5H-benzo[ij]quinolizine-2-carboxylic acid hydrochloride as white amorphous crystals having a melting point of 300° C. or more.

REFERENCE EXAMPLES 26 TO 28

In the same manner as described in Reference Example 25, the following compounds having various substituents shown in Table 4 below were prepared. The melting point and the crystal form of the resulting products are also shown in Table 4.

TABLE 4

| Reference Example No. | $R^2$ | $R^3$ | Color and Form of Crystal | HA | Melting Point (°C.) |
|---|---|---|---|---|---|
| 26 | O | H | White needle | — | >300 |
| 27 | HC—O | H | White needle | — | 285–287 |
| 28 | CH$_3$C—CH$_3$SO$_2$— | H | White needle | — | >300 |

REFERENCE EXAMPLE 29

19.5 g of 8-chloro-5-methyl-6,7-dihydro-1-oxo-1H,5H-benzo[ij]quinolizine-2-carboxylic acid and 35.5 g of piperazine were added to 350 ml of anhydrous dimethyl sulfoxide and the mixture was heated on an oil bath at 170° to 180° C. for 6 hours while stirring. Treatment of the reaction mixture in the same manner as in Reference Example 25 gave 5.3 g of 8-(1-piperazinyl)-5-methyl-6,7-dihydro-1-oxo-1H,5H-benzo[ij]quinolizine-2-carboxylic acid hydrochloride as white amorphous crystals having a melting point of 300° C. or more.

REFERENCE EXAMPLE 30

5.5 g of 4-chlorooxindole was dissolved in 80 ml of dioxane and 6.2 g of sodium borohydride was suspended in the resulting solution. 12.7 ml of trifluoroacetic acid (d=1.48) was added thereto dropwise at room temperature while stirring. After heat-refluxing the mixture for 4.5 hours, the solvent was removed therefrom under reduced pressure. Water was added to the residue and the water-insoluble materials were removed by filtration and washed with diethyl ether. The filtrate was extracted with diethyl ether and the ether layer was dried over anhydrous sodium sulfate followed by removing the solvent. The residue was distilled under reduced pressure to obtain 3.9 g of 4-chloroindoline as a colorless oily product having a boiling point of 135° C. at 10 mm Hg.

REFERENCE EXAMPLE 31

5 g of sodium borohydride was added to 66 ml of pyridine having dissolved therein 4.4 g of 2-methyl-4-chloroindole. To the mixture were added gradually 10.6 g of fine powders of aluminum chloride while ice-cooling with stirring. After completion of addition, the mixture was stirred and allowed to react at room temperature for 27 hours, the solvent was removed therefrom under reduced pressure. Water was added to the residue and the mixture was extracted with 100 ml of benzene. The benzene layer was washed with a saturated aqueous sodium chloride solution followed by concentrating. To the residue was added a 10% aqueous hydrochloric acid which caused foaming. After foaming ceased, the mixture was rendered neutral with an aqueous sodium carbonate solution followed by extracting the mixture with 100 ml of benzene. The benzene layer was dried over anhydrous sodium sulfate. After removing the solvent under reduced pressure, the extract was purified through a silica gel column chromatography (eluant:chloroform) to obtain 3.4 g of 2-methyl-4-chloroindoline which was confirmed by NMR.

REFERENCE EXAMPLE 32

4.4 g of diethyl ethoxymethylenemalonate was added to 3 g of 4-chloroindoline and the mixture was heated on an oil bath at 110° to 120° C. during which time liberation of ethanol was observed. 20 g of polyphosphoric acid prepared from 10 g of phosphoric acid and 10 g of phosphorus pentoxide was added thereto and the mixture was heated on an oil bath at 130° to 140° C. for 40 minutes. After completion of the reaction, the mixture was allowed to cool to 60° C., poured into water and rendered neutral with a 10% aqueous sodium hydroxide solution. The crystals precipitated were collected by filtration and washed with water. The crystals thustreated were mixed with 50 ml of a 10% aqueous sodium hydroxide solution and the mixture was heat-refluxed on an oil bath for 1 hour. As the reaction proceeded the mixture changed to a uniform solution. The solution was treated with activated carbon while hot followed by filtration. The filtrate was rendered acidic with concentrated hydrochloric acid to obtain 3.5 g of 9-chloro-6-oxo-1,2-dihydro-6H-pyrrolo[3,2,1-ij]quinoline-5-carboxylic acid. Recrystallization of the product from dimethylformamide gave 3.5 g of white needles having a melting point of 307.5° C. (decomposition).

REFERENCE EXAMPLE 33

4.4 g of diethyl ethoxymethylenemalonate was added to 3.4 g of 2-methyl-4-chloroindoline and the mixture was heated on an oil bath at 110° to 120° C. for 40 minutes. 20 g of polyphosphoric acid prepared from 10 g of phosphoric acid and 10 g of phosphorus pentoxide was added thereto and the mixture was heated on an oil bath at 130° to 140° C. for 1 hour. After completion of the reaction, the mixture was allowed to cool to 60° C., poured into ice water and rendered neutral with a 10% aqueous sodium hydroxide solution. The crystals precipitated were collected by filtration and washed with water. The crystals thus-treated were mixed with 50 ml of a 10% aqueous sodium hydroxide solution and the mixture was heat-refluxed on an oil bath for 1 hour. As the reaction proceeded the mixture was changed to a uniform solution. The solution was treated with activated carbon while hot followed by filtration. The filtrate was rendered acidic with concentrated hydrochloric acid to obtain 3.8 g of 9-chloro-2-methyl-6-oxo-1,2-dihydro-6H-pyrrolo[3,2,1-ij]quinoline-5-carboxylic acid. Recrystallization of the product from dimethylformamide gave 3.8 g of white needles having a melting point of 288° to 290° C.

REFERENCE EXAMPLE 34

20 ml of dimethyl sulfoxide were added to a mixture of 3 g of 9-chloro-6-oxo-1,2-dihydro-6H-pyrrolo[3,2,1-ij]quinoline-5-carboxylic acid and 6 g of anhydrous piperazine and the mixture was heated on an oil bath at 140° to 150° C. for 6 hours. After completion of reaction, the solvent was removed therefrom under reduced pressure and 50 ml of water was added to the residue to dissolve it. The solution was shaken with 100 ml of chloroform and the water layer was separated and treated with activated carbon. The aqueous solution was rendered acidic with a 10% aqueous hydrochloric acid and filtered. The filtrate was again treated with activated carbon followed by concentration. The addition of ethanol to the concentrate gave rise to crystals which were recrystallized from ethanol-water to obtain 1.5 g of 9-(1-piperazinyl)-6-oxo-1,2-dihydro-6H-pyrrolo[3,2,1-ij]quinoline-5-carboxylic acid hydrochloride as light yellow needles having a melting point of 300° C. or more.

REFERENCE EXAMPLE 35

20 ml of dimethyl sulfoxide was added to a mixture of 1.6 g of 9-chloro-2-methyl-6-oxo-1,2-dihydro-6H-pyrrolo[3,2,1-ij]quinoline-5-carboxylic acid and 3 g of anhydrous piperazine and the mixture was heated on an oil bath at 140° to 150° C. for 6 hours. After completion of the reaction, the solvent was removed therefrom under reduced pressure and 50 ml of water was added to the residue to dissolve it. The solution was shaken with 100 ml of chloroform and the water layer was separated and treated with activated carbon. The aqueous solution was rendered acidic with a 10% aqueous hydrochloric acid and filtered. The filtrate was again treated with activated carbon followed by concentration. The addition of ethanol to the concentrate gave rise to crystals which were recrystallized from ethanol-water to obtain 0.9 g of 9-(1-piperazinyl)-2-methyl-6-oxo-1,2-dihydro-6H-pyrrolo[3,2,1-ij]quinoline-5-carboxylic acid hydrochloride as light yellow needles having a melting point of 269°-273° C. (decomposition).

EXAMPLE 1

1.2 g of 7a,8,9,10,11,11a-hexahydro-4-oxo-4H-pyrido[3,2,1-jk]carbazole-5-carboxylic acid was dissolved in 75 ml of methylene chloride and 0.69 ml of triethylamine and 0.65 g of isobutyl chloroformate were added dropwise in this order while ice-cooling. After completion of addition, the mixture was allowed to react for 30 minutes while ice-cooling and 100 ml of a 3% sodium hydrogen carbonate having dissolved therein 2.1 g of D-(—)-α-aminobenzylpenicillanic acid.3H$_2$O was added thereto dropwise. After completion of addition, the mixture was allowed to react for 1 hour while ice-cooling and then at room temperature for 6 hours. As the reaction proceeded the reaction mixture was changed to a white suspension. The water layer was separated by centrifugation and adjusted to a pH of 2 with a 6 N hydrochloric acid to form light yellow precipitates which were extracted with 100 ml of methylene chloride. The methylene chloride layer was washed with water, dried over anhydrous sodium sulfate and concentrated to obtain 0.8 g of 6-[D-(—)-2-(7a,8,9,10,11,11a-hexahydro-4-oxo-4H-pyrido[3,2,1-jk]carbazole-5-carboxamide)-2-phenylacetamido]-3,3-dimethyl-7-oxo-4-thia-1-azabicyclo[3,2,0]heptane-2-carboxylic acid as white amorphous crystals having a melting point of 212° to 215° C. (decomposition).

EXAMPLE 2

1.3 g of 2-fluoro-7a,8,9,10,11,11a-hexahydro-4-oxo-4H-pyrido[3,2,1-jk]carbazole-5-carboxylic acid was dissolved in 75 ml of methylene chloride and 0.70 ml of triethylamine and 0.7 g of isobutyl chloroformate were added dropwise in this order while ice-cooling. After completion of addition, the mixture was allowed to react for 30 minutes while ice-cooling and 100 ml of a 3% sodium hydrogen carbonate having dissolved therein 2.1 g of D-(—)-α-aminobenzylpenicillanic acid.3H$_2$O was added thereto dropwise. After completion of addition, the mixture was allowed to react for 1 hour while ice-cooling and then at room temperature for 6 hours. As the reaction proceeded, the reaction mixture changed to a white suspension. The water layer was separated by centrifugation and adjusted to a pH of 2 with a 6 N hydrochloric acid to form white precipitates which were dissolved in 50 ml of a 3% aqueous sodium hydrogen carbonate solution and adjusted to pH 2 with 6 N hydrochloric acid to precipitate crystals, which were washed with water and dried to obtain 1.2 g of 6-[D-(—)-2-(2-fluoro-7a,8,9,10,11,11a-hexahydro-4-oxo-4H-pyrido[3,2,1-jk]carbazole-5-carboxamido)-2-phenylacetamido]-3,3-dimethyl-7-oxo-4-thia-1-azabicyclo[3,2,0]heptane-2-carboxylic acid as white amorphous crystals having a melting point of 238° to 240° C. (decomposition).

EXAMPLES 3 TO 12

In the same manner as described in Example 2, the following compounds having various substituents shown in Table 5 were prepared. The melting point and the crystal form of the resulting products are also shown in Table 5 below.

TABLE 5

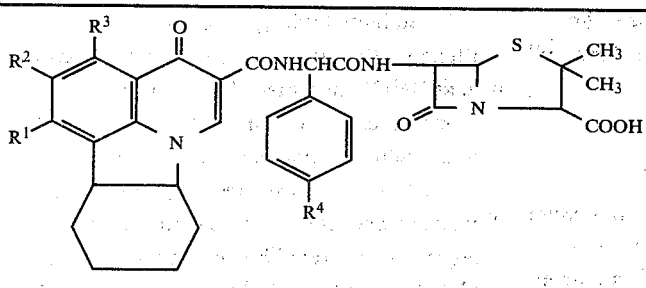

| Example No. | $R^1$ | $R^2$ | $R^3$ | $R^4$ | Color and Form of Crystal | Melting Point (°C.) |
|---|---|---|---|---|---|---|
| 3 | H | —CH$_3$ | H | H | White Amorphous | 203–206 (decomp.) |
| 4 | H | —OCH$_3$ | H | H | White Amorphous | 211–214 (decomp.) |
| 5 | —CH$_3$ | H | —CH$_3$ | H | White Amorphous | 198–200 (decomp.) |
| 6 | H | H | —NO$_2$ | H | Yellow Amorphous | 241–244 (decomp.) |
| 7 | H | H | —NHCOCH$_3$ | H | Brown Amorphous | 252–255 (decomp.) |
| 8 | H | —OH | H | H | White Amorphous | 229–232 (decomp.) |
| 9 | H | H | H | —OH | White Amorphous | 237–240 (decomp.) |
| 10 | H | H | —F | —OH | White Amorphous | 246–248 (decomp.) |
| 11 | H | —O(CH$_2$)$_3$CH$_3$ | H | H | White Amorphous | 193–196 (decomp.) |
| 12 | H | H | —NH$_2$ | H | Light Brown Amorphous | 248–251 (decomp.) |

EXAMPLE 13

1.1 g of 1-piperazinyl-7a,8,9,10,11,11a-hexahydro-4H-pyrido[3,2,1-jk]carbazole-4-oxo-5-carboxylic acid hydrochloride was added to 25 ml of dimethylformamide and 0.84 ml of triethylamine was added to the mixture while ice-cooling and stirred for 20 minutes. Then 0.4 ml of isobutyl chloroformate was added thereto dropwise and stirred for 1 hour while ice-cooling. On the other hand, 15 ml of dimethylformamide was added to a mixture of 1.3 g of ampicillin and 0.5 g of anhydrous magnesium sulfate and 0.7 ml of triethylamine was added dropwise to the resulting mixture while ice-cooling followed by allowing the mixture to react for 30 minutes. The reaction mixture was filtered and the filtrate was added at one time to the former reaction mixture and allowed to react for 2 hours while ice-cooling. After completion of the reaction, the reaction mixture was filtered and the filtrate was mixed with 2.5 ml of a 20% butanol solution of potassium 2-ethylhexanoate and the mixture was stirred for 30 minutes while ice-cooling. The addition of 300 ml of diethyl ether gave 1.2 g of potassium 6-{2-[1-(1-piperazinyl)-7a,8,9,10,11,-11a-hexahydro-4H-pyrido[3,2,1-jk]carbazole-4-oxo-5-carboxamido]-2-phenylacetamido}-3,3-dimethyl-7-oxo-4-thia-1-azabicyclo[3,2,0]heptane-2-carboxylate as white amorphous crystals having a melting point of 261° to 265° C. (decomposition).

EXAMPLE 14

1.1 g of 1-piperazinyl-7a,8,9,10,11,11a-hexahydro-4H-pyrido[3,2,1-jk]carbazole-4-oxo-5-carboxylic acid hydrochloride was added to 25 ml of dimethylformamide and 0.84 ml of triethylamine was added to the mixture while ice-cooling and stirred for 20 minutes. Then 0.4 ml of isobutyl chloroformate was added thereto dropwise and stirred for 1 hour while ice-cooling. On the other hand, 15 ml of dimethylformamide was added to a mixture of 1.3 g of amoxicillin and 0.5 g of anhydrous magnesium sulfate and 0.7 ml of triethylamine was added dropwise to the resulting mixture while ice-cooling followed by allowing the mixture to react for 30 minutes. The reaction mixture was filtered and the filtrate was added at one time to the former reaction mixture and allowed to react for 2 hours while ice-cooling. After completion of the reaction, the reaction mixture was filtered and the filtrate was mixed with 2.5 ml of a 20% butanol solution of potassium 2-ethylhexanoate and the mixture was stirred for 30 minutes while ice-cooling. The addition of 300 ml of diethyl ether gave 1.5 g of potassium 6-{2-[1-(1-piperazinyl)-7a,8,9,10,11,11a-hexahydro-4H-pyrido[3,2,1-jk]carbazole-4-oxo-5-carboxamido]-2-(4-hydroxyphenyl)acetamido}-3,3-dimethyl-7-oxo-4-thia-1-azabicyclo[3,2,0]heptane-2-carboxylate as white amorphous crystals having a melting point of 284° to 289° C. (decomposition).

EXAMPLE 15

(a) 1.44 g of 2-fluoro-7a,8,9,10,11,11a-hexahydro-4-oxo-4H-pyrido[3,2,1-jk]carbazole-5-carboxylic acid was suspended in 20 ml of methylene chloride and 0.85 ml of triethylamine was added to the suspension while ice-cooling followed by allowing the mixture to react for 10 minutes. Then, 0.85 ml of isobutyl chloroformate was added thereto dropwise and allowed to react for 30 minutes at the same temperature as above. To the reaction mixture were added 10 ml of a 10% aqueous sodium hydroxide solution having dissolved therein 0.9 g of D-(—)-phenyl-glycine at the same temperature as above and then 80 ml of dimethylformamide followed by allowing the mixture to react for 3 hours. After completion of the reaction, the reaction mixture was rendered neutral with a 6 N hydrochloric acid and the solvent was removed under reduced pressure. 20 ml of water and 100 ml of a 10% aqueous sodium hydroxide solution were added to the residue to dissolve it and the solution was treated with activated carbon and filtered. The filtrate was adjusted to a pH of 2 with concentrated hydrochloric acid to obtain light yellow crystals, which were washed with water, dried, mixed with 50 ml of chloroform with stirring and filtered. The filtrate was allowed to stand to obtain 1.2 g of D-(−)-2-(2-fluoro-7a,8,9,10,11,11a-hexahydro-4-oxo-4H-pyrido[3,2,1-jk]carbazole-5-carboxamido)phenylacetic acid as white needles having a melting point of 182° to 183° C.

(b) 2.1 g of D-(−)-2-(2-fluoro-7a,8,9,10,11,11a-hexahydro-4-oxo-4H-pyrido[3,2,1-jk]carbazole-5-carboxamido)phenylacetic acid was added in 50 ml of purified acetone and 0.85 ml of triethylamine was added thereto while ice-cooling. After stirring the mixture for 30 minutes, 0.85 g of isobutyl chloroformate was added thereto dropwise at the same temperature as above. The mixture was allowed to react at the same temperature as above for 30 minutes during which time precipitation of triethylamine hydrochloride was observed. The reaction mixture was cooled to −30° C. and stirred vigorously followed by adding thereto 45 ml of a 3% aqueous sodium hydrogen carbonate solution having dissolved therein 1.3 g of 6-aminopenicillanic acid. The mixture was allowed to react at below 0° C. for 40 minutes, 0° C. for 30 minutes and at room temperature for 10 minutes sequentially. After completion of the reaction, 100 ml of methylene chloride was added to the reaction mixture for extraction and the water layer was separated. The water layer was adjusted to a pH of 2 with a 6 N hydrochloric acid to obtain white precipitates, which were filtered and dissolved in 100 ml of methylene chloride and insoluble materials were removed. The solution was dried over anhydrous sodium sulfate followed by the removal of the solvent under reduced pressure whereby white powders were obtained. Recrystallization of the powders from dioxane-petroleum ether gave 1.2 g of 6-[D-(−)-2-(2-fluoro-7a,8,9,10,11,11a-hexahydro-4-oxo-4H-pyrido[3,2,1-jk]carbazole-5-carboxamido)-2-phenylacetamido]-3,3-dimethyl-7-oxo-4-thia-1-azabicyclo[3,2,0]heptane-2-carboxylic acid having a melting point of 238° to 240° C. (decomposition).

EXAMPLE 16

(a) 1.34 g of 7a,8,9,10,11,11a-hexahydro-4-oxo-4H-pyrido[3,2,1-jk]carbazole-5-carboxylic acid was suspended in 20 ml of methylene chloride and 0.85 ml of triethylamine was added to the suspension while ice-cooling followed by allowing the mixture to react for 10 minutes. Then, 0.85 ml of isobutyl chloroformate was added thereto dropwise and allowed to react for 30 minutes at the same temperature as above. To the reaction mixture were added 110 ml of a 10% aqueous sodium hydroxide solution having dissolved therein 0.9 g of D-(−)-phenylglycine at the same temperature as above and then 80 ml of dimethylformamide followed by allowing the mixture to react for 3 hours. After completion of the reaction, the reaction mixture was rendered neutral with a 6 N hydrochloric acid and the solvent was removed under reduced pressure. 20 ml of water and 100 ml of a 10% aqueous sodium hydroxide solution were added to the residue to dissolve it and the solution was treated with activated carbon and filtered. The filtrate was adjusted to a pH of 2 with concentrated hydrochloric acid to obtain light yellow crystals, which were washed with water, dried, mixed with 50 ml of chloroform with stirring and filtered. The filtrate was mixed with 30 ml of petroleum ether to obtain 1.1 g of D-(−)-7a,8,9,10,11,11a-hexahydro-4-oxo-4H-pyrido[3,2,1-jk]carbazole-5-carboxamido)phenylacetic acid as light yellow needles having a melting point of 165° to 167° C.

(b) 2.0 g of D-(−)-2-7a,8,9,10,11,11a-hexahydro-4-oxo-4H-pyrido[3,2,1-jk]carbazole-5-carboxamido)-phenylacetic acid was added in 50 ml of purified acetone and 0.85 ml of triethlamine was added thereto while ice-cooling. After stirring the mixture for 30 minutes, it was allowed to react at the same temperature as above for 30 minutes during which time precipitation of triethylamine hydrochloride was observed. The reaction mixture was cooled to −30° C. and stirred vigorously followed by adding thereto 45 ml of a 3% aqueous sodium hydrogen carbonate solution having dissolved therein 1.3 g of 6-aminopenicillanic acid. The mixture was allowed to react at below 0° C. for 40 minutes, 0° C. for 30 minutes and at room temperature for 10 minutes sequentially. After completion of the reaction, 100 ml of methylene chloride was added to the reaction mixture for extraction (when the reaction mixture was in a state of suspension the suspension was centrifuged) and the water layer was separated. The water layer was adjusted to a pH of 2 with a 6 N hydrochloric acid to obtain light yellow precipitates which were filtered and dissolved in 100 ml of methylene chloride and insoluble materials were removed. The solution was dried over anhydrous sodium sulfate followed by the removal of the solvent under reduced pressure whereby light yellow powders were obtained. Recrystallization of the powders from dioxane-petroleum ether gave 1.1 g of 6-[D-(−)-2-(7a,8,9,10,11,11a-hexahydro-4-oxo-4H-pyrido[2,3,1-jk]carbazole-5-carboxamido)-2-phenylacetamido]-3,3-dimethyl-7-oxo-4-thia-1-azabicyclo[3,2,0]heptane-2-carboxylic acid as white amorphous crystals having a melting point of 212° to 215° C. (decomposition).

EXAMPLES 17 TO 26

In the same manner as described in Example 16, the following compounds having various substituents shown in Table 6 were prepared. The melting point and the crystal form of the resulting products are also shown in Table 6 below.

TABLE 6

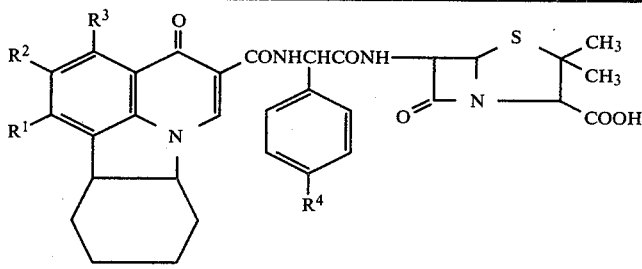

| Example No. | R¹ | R² | R³ | R⁴ | Color and Form of Crystal | Melting Point (°C.) |
|---|---|---|---|---|---|---|
| 17 | H | —CH₃ | H | H | White Amorphous | 203–206 (decomp.) |
| 18 | H | —OCH₃ | H | H | White Amorphous | 211–214 (decomp.) |
| 19 | —CH₃ | H | —CH₃ | H | White Amorphous | 198–200 (decomp.) |
| 20 | H | H | —NO₂ | H | Yellow Amorphous | 241–244 (decomp.) |
| 21 | H | H | —NHCOCH₃ | H | Brown Amorphous | 252–255 (decomp.) |
| 22 | H | —OH | H | H | White Amorphous | 229–232 (decomp.) |
| 23 | H | H | H | —OH | White Amorphous | 237–240 (decomp.) |
| 24 | H | H | —NH₂ | H | Light Brown Amorphous | 248–251 (decomp.) |
| 25 | HN⌒N— | H | H | H | White Amorphous | 261–265 (decomp.) |
| 26 | HN⌒N— | H | H | —OH | White Amorphous | 284–289 (decomp.) |

EXAMPLE 27

2.28 g of 6,7-dihydro-1-oxo-1H,5H-benzo[ij]quinolizine-2-carboxylic acid was dissolved in 80 ml of methylene chloride and 1.65 ml of triethylamine and 1.65 g of isobutyl chloroformate were added dropwise in this order while ice-cooling. After completion of addition, the mixture was allowed to react for 30 minutes while ice-cooling and a mixture of 20 ml of methylene chloride and 3 ml of triethylamine having suspended therein 4.1 g of D-(—)-α-aminobenzylpenicillin.3H₂O was added thereto at a time while cooling. The mixture was allowed to react for 2.5 hours while ice-cooling to form a uniform solution, which was adjusted to a pH of 7 with glacial acetic acid and then shaken with 70 ml of water to wash out triethylamine hydrochloride. 100 ml of a 3% aqueous sodium hydrogen carbonate was added to the methylene chloride layer and the mixture was shaken to form a white suspension. The water layer was separated by centrifugation and adjusted to a pH of 2 with a 6 N hydrochloric acid to form white precipitates which were washed with water and dried under reduced pressure to obtain 3.5 g of 6-[D-(—)-2-(6,7-dihydro-1-oxo-1H,5H-benzo[ij]quinolizine-2-carboxamide)-2-phenylacetamido]-3,3-dimethyl-7-oxo-4-thia-1-azabicyclo[3,2,0]heptane-2-carboxylic acid as white amorphous crystals having a melting point of 195° to 197° C. (decomposition).

EXAMPLE 28

1.32 g of 9-chloro-6,7-dihydro-1-oxo-1H,5H-benzo[ij]quinolizine-2-carboxylic acid was dissolved in 50 ml of acetone and 0.75 ml of triethylamine and 0.75 g of isobutyl chloroformate were added dropwise in this order while ice-cooling. After completion of addition, the mixture was allowed to react for 30 minutes while ice-cooling and a mixture of 10 ml of methylene chloride and 1.5 ml of triethylamine having suspended therein 2.0 g of D-(—)-α-aminobenzylpenicillin.3H₂O was added thereto at a time while cooling. The mixture was allowed to react for 2 hours while ice-cooling followed by concentration under reduced pressure on a water bath at 35° to 40° C. 100 ml of a 7% aqueous sodium carbonate solution was added to the concentrate and the mixture was filtered. The filtrate was adjusted to a pH of 2 with a 6 N hydrochloric acid to form white precipitates, which were washed with water and dried under reduced pressure to obtain 1.1 g of 6-[D-(—)-2--(9-chloro-6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid as white amorphous crystals having a melting point of 220° to 223° C. (decomposition).

EXAMPLES 29 TO 41

In the same manner as described in Example 28, the following compounds having various substituents shown in Table 7 were prepared. The melting point and the crystal form of the resulting products are also shown in Table 7 below.

TABLE 7

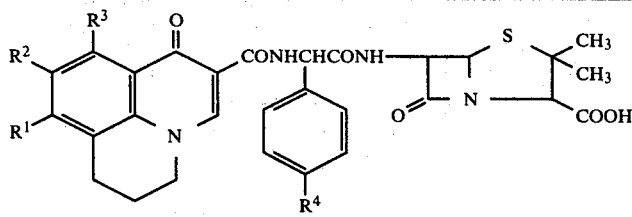

| Example No. | R¹ | R² | R³ | R⁴ | Color and Form of Crystal | Melting Point (°C.) |
|---|---|---|---|---|---|---|
| 29 | H | —OCH₃ | H | H | White Amorphous | 198–201 (decomp.) |
| 30 | —Cl | H | —Cl | H | White Amorphous | 205–208 (decomp.) |
| 31 | H | —F | H | H | White Amorphous | 216–218 (decomp.) |
| 32 | H | H | —NO₂ | H | Yellow Amorphous | 230–233 (decomp.) |
| 33 | H | H | —NH₂ | H | Light Brown Amorphous | 239–241 (decomp.) |
| 34 | H | H | —NHCOCH₃ | H | Yellow Amorphous | 243–246 (decomp.) |
| 35 | H | H | —NHCO(CH₂)₂CH₃ | H | Yellow Amorphous | 225–228 (decomp.) |
| 36 | H | —CH₃ | H | H | White Amorphous | 203–205 (decomp.) |
| 37 | H | —(CH₂)₃CH₃ | H | H | White Amorphous | 186–187 (decomp.) |
| 38 | H | —OH | H | H | White Amorphous | 234–237 (decomp.) |
| 39 | H | H | H | —OH | White Amorphous | 238–241 (decomp.) |
| 40 | H | —Cl | H | —OH | White Amorphous | 251–254 (decomp.) |
| 41 | —OSO₂CH₃ | H | H | H | White Amorphous | 190–192 (decomp.) |

EXAMPLE 42

2.4 g of 5-methyl-6,7-dihydro-1-oxo-1H,5H-benzo[ij]-quinolizine-2-carboxylic acid was suspended in 50 ml of anhydrous dimethylformamide and 1.66 ml of triethylamine was added to the mixture while ice-cooling and stirred for 15 minutes. Then, 1.6 ml of isobutyl chloroformate was added thereto dropwise and stirred for 45 minutes at the same temperature as above. On the other hand, 5 g of ampicillin was suspended in 60 ml of anhydrous dimethylformamide and 2.8 ml of triethylamine and 1 g of anhydrous magnesium sulfate were added to the suspension while ice-cooling and the mixture was stirred at the same temperature as above for 30 minutes and insoluble materials were removed by filtration. The triethylamine salt of ampicillin thus-obtained was added to the former reaction mixture and stirred for 2 hours while ice-cooling. After completion of the reaction, insoluble materials were removed by filtration and 10 ml of a 20% n-butanol solution of sodium 2-ethylhexanoate and then 500 ml of diethyl ether were added to the filtrate to precipitate crystals. The crystals were collected by filtration and dissolved in 300 ml of water and the solution was rendered acidic (pH=3) to form precipitates, which were washed with water and dried at room temperature under reduced pressure to obtain 5.2 g of 6-[2-(5-methyl-6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid as white amorphous crystals having a melting point of 203° to 205° C. (decomposition).

EXAMPLE 43

1.2 g of 5-methyl-6,7-dihydro-1-oxo-1H,5H-benzo[ij]-quinolizine-2-carboxylic acid was suspended in 25 ml of anhydrous dimethylformamide and 0.83 ml of triethylamine was added to the mixture while ice-cooling and stirred for 15 minutes. Then, 0.8 ml of isobutyl chloroformate was added thereto dropwise and stirred for 45 minutes at the same temperature as above. On the other hand, 2.5 g of amoxicillin was suspended in 30 ml of anhydrous dimethylformamide and 1.4 ml of triethylamine and 1 g of anhydrous magnesium sulfate were added to the suspension while ice-cooling and the mixture was stirred at the same temperature as above for 30 minutes and insoluble materials were removed by filtration. The triethylamine salt of amoxicillin thus-obtained was added to the former reaction mixture and stirred for 2 hours while ice-cooling. The resulting mixture was treated in the same manner as Example 42 to obtain 2.8 g of 6-[2-(5-methyl-6,7-dihydro-1-oxo-1H,5H-benzo[ij]-quinolizine-2-carboxamido)-2-(4-hydroxy)-phenylacetamido]-3,3-dimethyl-7-oxo-4-thia-1-azabicyclo[3,2,0]heptane-2-carboxylic acid as white amorphous crystals having a melting point of 199° to 201° C. (decomposition).

EXAMPLE 44

0.85 g of 8-(4-formyl-1-piperazinyl)-6,7-dihydro-1-oxo-1H,5H-benzo[ij]quinolizine-2-carboxylic acid was suspended in 25 ml of anhydrous dimethylformamide and 0.42 ml of triethylamine was added to the mixture while ice-cooling and stirred for 15 minutes. Then, 0.4 ml of isobutyl chloroformate was added thereto dropwise and stirred for 45 minutes at the same temperature as above. On the other hand, 1.3 g of ampicillin was suspended in 15 ml of anhydrous dimethylformamide and 0.7 ml of triethylamine and 0.5 g of anhydrous magnesium sulfate were added to the suspension while ice-cooling and the mixture was stirred at the same temperature as above for 30 minutes and insoluble materials were removed by filtration. The triethylamine salt of ampicillin thus-obtained was added to the former reaction mixture and stirred for 2 hours while ice-cooling. After completion of the reaction, insoluble materials were removed by filtration and 2.5 ml of a 20% n-butanol solution of sodium 2-ethylhexanoate and then 200 ml of diethyl ether were added to the filtrate to precipitate crystals. The crystals were collected by filtration and dissolved in 100 ml of water and the solution was rendered acidic (pH=2) to form precipitates which were washed with water and dried at room temperature under reduced pressure to obtain 0.87 g of 6-{2-[8-(4-formyl-1-piperazinyl)-6,7-dihydro-1-oxo-1H,5H-benzo[ij]quinolizine-2-carboxamido]-2-phenylacetamido}-3,3-dimethyl-7-oxo-4-thia-1-azabicyclo[3,2,0]heptane-2-carboxylic acid as white amorphous crystals having a melting point of 217° to 224° C. (decomposition).

EXAMPLE 45

0.85 g of 8-(4-formyl-1-piperazinyl)-6,7-dihydro-1-oxo-1H,5H-benzo[ij]quinolizine-2-carboxylic acid was suspended in 25 ml of anhydrous dimethylformamide and 0.42 ml of triethylamine was added to the mixture while ice-cooling and stirred for 15 minutes. Then, 0.4 ml of isobutyl chloroformate was added thereto dropwise and stirred for 45 minutes at the same temperature as above. On the other hand, 1.3 g of amoxicillin was suspended in 15 ml of anhydrous dimethylformamide and 0.7 ml of triethylamine and 0.5 g of anhydrous magnesium sulfate were added to the suspension while ice-cooling and the mixture was stirred at the same temperature as above for 30 minutes and insoluble materials were removed by filtration. The triethylamine salt of amoxicillin thus-obtained was added to the former reaction mixture and stirred for 2 hours while ice-cooling. The resulting mixture was treated in the same manner as Example 44 to obtain 1.0 g of 6-{2-[8-(4-formyl-1-piperazinyl)-6,7-dihydro-1-oxo-1H,5H-benzo[ij]quinolizine-2-carboxamido]-2-(4-hydroxy)phenylacetamido}-3,3-dimethyl-7-oxo-4-thia-1-azabicyclo[3,2,0]heptane-2-carboxylic acid as white amorphous crystals having a melting point of 249° to 254° C. (decomposition).

EXAMPLE 46

0.78 g of 8-(1-piperazinyl)-6,7-dihydro-1-oxo-1H,5H-benzo[ij]quinolizine-2-carboxylic acid was suspended in 25 ml of anhydrous dimethylformamide and 0.42 ml of triethylamine was added to the mixture while ice-cooling and stirred for 15 minutes. Then, 0.4 ml of isobutyl chloroformate was added thereto dropwise and stirred for 45 minutes at the same temperature as above. On the other hand, 1.3 g of ampicillin was suspended in 15 ml of anhydrous dimethylformamide and 0.7 ml of triethylamine and 0.5 g of anhydrous magnesium sulfate were added to the suspension while ice-cooling and the mixture was stirred at the same temperature as above for 30 minutes and insoluble materials were removed by filtration. The triethylamine salt of ampicillin thus-obtained was added to the former reaction mixture and stirred for 2 hours while ice-cooling. After completion of the reaction, insoluble materials were removed by filtration and 2.5 ml of a 20% n-butanol solution of potassium 2-ethylhexanoate and then 300 ml of diethyl ether were added to the filtrate to precipitate crystals to obtain 0.97 g of potassium 6-{2-[8-(1-piperazinyl)-6,7-dihydro-1-oxo-1H,5H-benzo[ij]quinolizine-2-carboxamido]-2-phenylacetamido}-3,3-dimethyl-7-oxo-4-thia-1-azabicyclo[3,2,0]heptane-2-carboxylate as light yellow amorphous crystals having a melting point of 218° to 225° C. (reddening); 245° to 250° C. (decomposition).

EXAMPLE 47

0.78 g of 8-(1-piperazinyl)-6,7-dihydro-1-oxo-1H,5H-benzo[ij]quinolizine-2-carboxylic acid was suspended in 25 ml of anhydrous dimethylformamide and 0.42 ml of triethylamine was added to the mixture while ice-cooling and stirred for 15 minutes. Then, 0.4 ml of isobutyl chloroformate was added thereto dropwise and stirred for 45 minutes at the same temperature as above. On the other hand, 1.3 g of amoxicillin was suspended in 15 ml of anhydrous dimethylformamide and 0.7 ml of triethylamine and 0.5 g of anhydrous magnesium sulfate were added to the suspension while ice-cooling and the mixture was stirred at the same temperature as above for 30 minutes and insoluble materials were removed by filtration. The triethylamine salt of amoxicillin thus-obtained was added to the former reaction mixture and stirred for 2 hours while ice-cooling. After completion of the reaction, insoluble materials were removed by filtration and 2.5 ml of a 20% n-butanol solution of sodium 2-ethylhexanoate and then 300 ml of diethyl ether were added to the filtrate to precipitate crystals. The crystals were collected by filtration and dissolved in 100 ml of water to remove a small amount of insoluble materials by filtration. The filtrate was frozen and dried to obtain 0.81 g of sodium 6-{2-[8-(1-piperazinyl)-6,7-dihydro-1-oxo-1H,5H-benzo[ij]quinolizine-2-carboxamido]2-(4-hydroxy)phenylacetamido}-3,3-dimethyl-7-oxo-4-thia-1-azabicyclo[3,2,0]heptane-2-carboxylate as white amorphous crystals.

Elemental Analysis for $C_{33}H_{36}N_6O_6S \cdot 5.5H_2O$

|  | C | H | N |
|---|---|---|---|
| Calcd. (%): | 53.25 | 6:32 | 11.29 |
| Found (%): | 52.97 | 6.12 | 11.08 |

EXAMPLE 48

0.7 g of 8-(4-acetyl-1-piperazinyl)-6,7-dihydro-1-oxo-1H,5H-benzo[ij]quinolizine-2-carboxylic acid was suspended in 20 ml of anhydrous dimethylformamide and 0.34 ml of triethylamine was added to the mixture while ice-cooling and stirred for 15 minutes. Then, 0.32 ml of isobutyl chloroformate was added thereto dropwise and stirred for 45 minutes at the same temperature as above. On the other hand, 1 g of ampicillin was suspended in 10 ml of anhydrous dimethylformamide and 0.56 ml of triethylamine and 0.4 g of anhydrous magnesium sulfate were added to the suspension while ice-cooling and the mixture was stirred at the same temperature as above for 30 minutes and insoluble materials were removed by filtration. The triethylamine salt of ampicillin thus-obtained was added to the former reaction mixture and stirred for 2 hours while ice-cooling. The resulting mixture was treated in the same manner as Example 44 to obtain 0.75 g of 6-{2-[8-(4-acetyl-1-piperazinyl)-6,7-dihydro-1-oxo-1H,5H-benzo[ij]quinolizine-2-carboxamido]-2-(4-hydroxy)phenylacetamido}-3,3-dimethyl-7-oxo-4-thia-1-azabicyclo[3,2,0]heptane-2-carboxylic acid as white amorphous crystals having a melting point of 214° to 219° C. (decomposition).

EXAMPLE 49

0.81 g of 8-(4-methanesulfonyl-1-piperazinyl)-6,7-dihydro-1-oxo-1H,5H-benzo[ij]quinolizine-2-carboxylic acid was suspended in 25 ml of anhydrous dimethylformamide and 0.42 ml of triethylamine was added to the mixture while ice-cooling and stirred for 15 minutes. Then, 0.4 ml of isobutyl chloroformate was added thereto dropwise and stirred for 45 minutes at the same temperature as above. On the other hand, 1.3 g of ampicillin was suspended in 15 ml of anhydrous dimethylformamide and 0.7 ml of triethylamine and 0.5 g of anhydrous magnesium sulfate were added to the suspension while ice-cooling and the mixture was stirred at the same temperature as above for 30 minutes and insoluble materials were removed by filtration. The triethylamine salt of ampicillin thus-obtained was added to the former reaction mixture and stirred for 2 hours while ice-cooling followed by treating the resulting mixture in the same manner as in Example 44 to obtain 1.25 g of 6-{2-[8-(4-methanesulfonyl-1-piperazinyl)-6,7-dihydro-1-oxo-1H,5H-benzo[ij]quinolizine-2-carboxamido]-2-phenylacetamido}-3,3-dimethyl-7-oxo-4-thia-1-azabicyclo[3,2,0]heptane-2-carboxylic acid as white amorphous crystals having a melting point of 182° to 187° C. (decomposition).

EXAMPLE 50

(a) 2.3 g of 6,7-dihydro-1-oxo-1H,5H-benzo[ij]quinolizine-2-carboxylic acid was suspended in 30 ml of dimethylformamide and 1.65 ml of triethylamine was added to the suspension while ice-cooling followed by allowing the mixture to react for 10 minutes. Then, 5 ml of dimethylformamide having dissolved therein 1.65 g of isobutyl chloroformate was added thereto dropwise and allowed to react for 30 minutes at the same temperature as above to form a uniform solution. To the reaction mixture were added at a time 10 ml of a 10% aqueous sodium hydroxide solution having dissolved therein 2 g of D-(−)-phenylglycine at the same temperature as above and then the mixture was allowed to react at room temperature for 3 hours. After completion of the reaction, the reaction mixture was concentrated under reduced pressure and 70 ml of water was added thereto to form precipitates which were removed by filtration. The filtrate was adjusted to a pH of 2 with concentrated hydrochloric acid while ice-cooling to obtain white crystals, which were filtered, washed with water and dried to obtain 2.6 g of D-(−)-2-(6,7-dihydro-1-oxo-1H,5H-benzo[ij]quinolizine-2-carboxamido)phenylacetic acid having a melting point of 219° to 220° C.

(b) 1.8 g of D-(−)-2-(6,7-dihydro-1-oxo-1H,5H-benzo[ij]quinolizine-2-carboxamido)phenylacetic acid was added in 50 ml of purified acetone and 0.8 ml of triethylamine was added thereto while ice-cooling. After stirring the mixture for 30 minutes, 0.8 g of isobutyl chloroformate was added dropwise thereto and the mixture was allowed to react at the same temperature as above for 30 minutes, during which time precipitation of triethylamine hydrochloride was observed. The reaction mixture was cooled to −30° C. and stirred vigorously followed by adding thereto 45 ml of a 3% aqueous sodium hydrogen carbonate solution having dissolved therein 1.3 g of 6-aminopenicillanic acid. The mixture was allowed to react at below 0° C. for 40 minutes, 0° C. for 30 minutes and at room temperature for 20 minutes sequentially. After completion of the reaction, the reaction mixture was adjusted to a pH of 7 with glacial acetic acid and concentrated under reduced pressure. 50 ml of a 3% aqueous sodium hydrogen carbonate was added to the concentrate followed by filtration. The filtrate was adjusted to a pH of 2 with a 6 N hydrochloric acid while ice-cooling to form precipitates, which were separated by filtration and washed with water (pH=5 to 6). Purification of the precipitates thus-treated by repeating the above-described procedure (3% aqueous sodium hydrogen carbonate solution-6 N hydrochloric acid) gave 1.8 g of 6-[D-(−)-2-(6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid as white amorphous crystals having a melting point of 195° to 197° C. (decomposition).

EXAMPLE 51

(a) 1 g of 9-chloro-6,7-dihydro-1-oxo-1H,5H-benzo[ij]quinolizine-2-carboxylic acid was suspended in 20 ml of dimethylformamide and 0.7 ml of triethylamine was added to the suspension while ice-cooling. Then, 5 ml of dimethylformamide having dissolved therein 0.7 g of isobutyl chloroformate was added thereto dropwise at the same temperature as above and allowed to react for 30 minutes at the same temperature as above to form a uniform solution. To the reaction mixture was added at one time 4 ml of a 5% aqueous sodium hydroxide solution having dissolved therein 0.6 g of D-(−)-phenylglycine at the same temperature as above and then the mixture was allowed to react at room temperature for 3 hours. After completion of the reaction, the reaction mixture was concentrated under reduced pressure and 30 ml of water was added thereto to form precipitates which were removed by filtration. The filtrate was adjusted to a pH of 2 with concentrated hydrochloric acid while ice-cooling to obtain white crystals, which were filtered, washed with water and dried to obtain 0.9 g of D-(−)-2-(9-chloro-6,7-dihydro-1-oxo-1H,5H-benzo[ij]quinolizine-2-carboxamido)-phenylacetic acid having a melting point of 180° to 182° C.

(b) 2.0 g of D-(−)-2-(9-chloro-6,7-dihydro-1-oxo-1H,5H-benzo[ij]quinolizine-2-carboxamido)phenylacetic acid was added in 80 ml of purified acetone and 0.85 ml of triethylamine was added thereto while ice-cooling. After stirring the mixture for 30 minutes, 0.85 g of isobutyl chloroformate was added dropwise thereto at the same temperature and the mixture was allowed to react at the same temperature as above for 30 minutes, during which time precipitation of triethylamine hydrochloride was observed. The reaction mixture was cooled to −30° C. and stirred vigorously followed by adding thereto 45 ml of a 3% aqueous sodium hydrogen carbonate solution having dissolved therein 1.3 g of 6-aminopenicillanic acid. The mixture was allowed to react at below 0° C. for 40 minutes, 0° C. for 30 minutes and at room temperature for 20 minutes sequentially. After completion of the reaction, the reaction mixture was adjusted to a pH of 7 with glacial acetic acid and concentrated under reduced pressure. 50 ml of a 7% aqueous sodium hydrogen carbonate was added to the concentrate followed by filtration. The filtrate was adjusted to a pH of 2 with a 6 N hydrochloric acid while ice-cooling to give 1.2 g of 6-[D-(—)-2-(9-chloro-6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid as white amorphous crystals having a melting point of 220° to 223° C. (decomposition).

EXAMPLES 52 TO 69

In the same manner as described in Example 51, the following compounds having various substituents shown in Tables 8 and 9 were prepared. The melting point and the crystal form of the resulting products are also shown in Tables 8 and 9 below.

TABLE 8

| Example No. | $R^1$ | $R^2$ | $R^3$ | $R^4$ | Color and Form of Crystal | Melting Point (°C.) |
|---|---|---|---|---|---|---|
| 52 | H | —OCH₃ | H | H | White Amorphous | 198–201 (decomp.) |
| 53 | —Cl | H | —Cl | H | White Amorphous | 205–208 (decomp.) |
| 54 | H | —F | H | H | White Amorphous | 216–218 (decomp.) |
| 55 | H | H | —NO₂ | H | Yellow Amorphous | 230–233 (decomp.) |
| 56 | H | H | —NH₂ | H | Light Yellow Amorphous | 239–241 (decomp.) |
| 57 | H | H | —NHCOCH₃ | H | Yellow Amorphous | 243–246 (decomp.) |
| 58 | H | —CH₃ | H | H | White Amorphous | 203–205 (decomp.) |
| 59 | H | —OH | H | H | White Amorphous | 234–237 (decomp.) |
| 60 | H | H | H | —OH | White Amorphous | 238–241 (decomp.) |
| 61 | H | —Cl | H | —OH | White Amorphous | 251–254 (decomp.) |
| 62 | —OSO₂CH₃ | H | H | H | White Amorphous | 190–192 (decomp.) |

TABLE 9

| Example No. | $R^1$ | $R^2$ | $R^3$ | $R^4$ | $R^5$ | Color and Form of Crystal | Melting Point (°C.) |
|---|---|---|---|---|---|---|---|
| 63 | —CH₃ | H | H | H | H | White Amorphous | 203–205 (decomp.) |
| 64 | —CH₃ | H | H | H | —OH | White Amorphous | 199–201 (decomp.) |
| 65 | H | HC(=O)—N⌒N— | H | H | H | White Amorphous | 217–224 (decomp.) |
| 66 | H | HC(=O)—N⌒N— | H | H | —OH | White Amorphous | 249–254 (decomp.) |
| 67 | H | HN⌒N— | H | H | H | Light Yellow Amorphous | 218–225 (reddening) 245–250 (decomp.) |

TABLE 9-continued

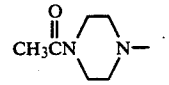

| Example No. | R¹ | R² | R³ | R⁴ | R⁵ | Color and Form of Crystal | Melting Point (°C.) |
|---|---|---|---|---|---|---|---|
| 68 | H | CH₃CN(=O)–N⟨⟩N– | H | H | H | White Amorphous | 214–219 (decomp.) |
| 69 | H | CH₃SO₂–N⟨⟩N– | H | H | H | White Amorphous | 182–187 (decomp.) |

EXAMPLE 70

2.2 g of 1,2-dihydro-6-oxo-6H-pyrrolo[3,2,1-ij]quinoline-5-carboxylic acid was dissolved in 80 ml of methylene chloride and 1.65 ml of triethylamine and 1.65 g of isobutyl chloroformate were added dropwise in this order while ice-cooling. After completion of addition, the mixture was allowed to react for 30 minutes while ice-cooling and a mixture of 20 ml of methylene chloride and 3 ml of triethylamine having suspended therein 4.1 g of D-(−)-α-aminobenzylpenicillin.3H₂O was added thereto at one time while cooling. The mixture was allowed to react for 2.5 hours while ice-cooling to form a uniform solution, which was adjusted pH value to a pH of 7 with glacial acetic acid and then shaken with 70 ml of water to wash out triethylamine hydrochloride. 100 ml of a 3% aqueous sodium hydrogen carbonate was added to the methylene chloride layer and the mixture was shaken to form a white suspension. The water layer was separated by centrifugation and adjusted to a pH of 2 with a 6 N hydrochloric acid to form white precipitates, which were washed with water and dried under reduced pressure to obtain 2.8 g of 6-[D-(−)-2-(1,2-dihydro-6-oxo-6H-pyrrolo[3,2,1-ij]quinoline-5-carboxamido)-2-phenylacetamido]-3,3-dimethyl-7-oxo-4-thia-1-azabicyclo[3,2,0]heptane-2-carboxylic acid as white amorphous crystals having a melting point of 215° to 218° C. (decomposition).

EXAMPLE 71

In the same manner as in Example 70, 6-[D-(−)-2-(8-methyl-1,2-dihydro-6-oxo-6H-pyrrolo[3,2,1-ij]quinoline-5-carboxamido)-2-phenylacetamido]-3,3-dimethyl-7-oxo-4-thia-1-azabicyclo[3,2,0]heptane-2-carboxylic acid was obtained as white amorphous crystals.

Elemental Analysis for $C_{29}H_{27}N_4O_6S$:

| | C | H | N |
|---|---|---|---|
| Calcd. (%): | 62.24 | 4.86 | 10.01 |
| Found (%): | 62.52 | 4.98 | 10.13 |

EXAMPLE 72

In the same manner as in Example 70, 6-[D-(−)-2-(7-nitro-1,2-dihydro-6-oxo-6H-pyrrolo[3,2,1-ij]quinoline-5-carboxamido)-2-phenylacetamido]-3,3-dimethyl-7-oxo-4-thia-1-azabicyclo[3,2,0]heptane-2-carboxylic acid was obtained as yellow amorphous crystals.

Elemental Analysis for $C_{28}H_{24}N_5O_8S$:

| | C | H | N |
|---|---|---|---|
| Calcd. (%): | 56.94 | 4.10 | 11.86 |
| Found (%): | 57.21 | 4.31 | 11.97 |

EXAMPLE 73

In the same manner as in Example 70, 6-[D-(−)-2-(-8-fluoro-1,2-dihydro-6-oxo-6H-pyrrolo[3,2,1-ij]quinoline-5-carboxamido)-2-(4-hydroxy)phenylacetamido]-3,3-dimethyl-7-oxo-4-thia-1-azabicyclo[3,2,0]heptane-2-carboxylic acid was obtained as white amorphous crystals.

Elemental Analysis for $C_{28}H_{24}N_4O_7SF$:

| | C | H | N |
|---|---|---|---|
| Calcd. (%): | 58.03 | 4.17 | 9.67 |
| Found (%): | 58.21 | 4.21 | 9.79 |

EXAMPLE 74

2.3 g of 6,7-dihydro-1-oxo-1H,5H-benzo[ij]quinolizine-2-carboxylic acid was suspended in 50 ml of anhydrous methylene chloride and 1.66 ml of triethylamine was added thereto and the mixture was stirred for 15 minutes while ice-cooling. Then, 1.6 g of isobutyl chloroformate was added dropwise thereto while ice-cooling. After completion of addition, the mixture was stirred for 45 minutes while ice-cooling. On the other hand, 4.5 g of cephaloglycine was suspended in 60 ml of anhydrous dimethylformamide and 2.8 ml of triethylamine and 1 g of magnesium sulfate were added to the suspension. The resulting mixture was stirred at the same temperature as above for 30 minutes and insoluble materials were removed by filtration. The solution of triethylamine salt of cephaloglycine thus-obtained was added to the former reaction mixture and stirred for 2 hours while ice-cooling.

After completion of the reaction, insoluble materials were removed by filtration and 10 ml of a 20% n-butanol solution of sodium 2-ethylhexanoate and then 500 ml of diethyl ether were added to the filtrate to precipitate crystals.

The crystals were collected by filtration and dissolved in 300 ml of water and the solution was rendered acidic (pH=3) to form precipitates, which were washed with water and dried at room temperature under reduced pressure to obtain 4.5 g of 7-[2-(6,7-dihydro-1-oxo-1H,5H-benzo[ij]quinolizine-2-carboxamido)-2-phenylacetamido]-3-(acetyloxymethyl)-8-oxo-5-thia-1-azabicyclo[4,2,0]oct-2-ene-2-carboxylic acid as white amorphous crystals having a melting point of 226° to 230° C. (decomposition).

EXAMPLE 75

2.4 g of 5-methyl-6,7-dihydro-1-oxo-1H,5H-benzo[ij]quinolizine-2-carboxylic acid was suspended in 50 ml of anhydrous dimethylformamide and 1.66 ml of triethylamine was added thereto and the mixture was stirred for 15 minutes while ice-cooling. Then, 1.6 ml of isobutyl chloroformate were added dropwise thereto while ice-cooling. After completion of addition, the mixture was stirred for 45 minutes while ice-cooling. On the other hand, 4.5 g of cephaloglycine was suspended in 60 ml of anhydrous dimethylformamide and 2.8 ml of triethylamine and 1 g of magnesium sulfate were added to the suspension. The resulting mixture was stirred at the same temperature as above for 30 minutes and insoluble materials were removed by filtration. The solution of triethylamine salt of cephaloglycine thus-obtained was added to the former reaction mixture and stirred for 2 hours while ice-cooling.

After completion of the reaction, insoluble materials were removed by filtration and 10 ml of a 20% n-butanol solution of sodium 2-ethylhexanoate and then 500 ml of diethyl ether were added to the filtrate to precipitate crystals. The crystals were collected by filtration and dissolved in 300 ml of water and the solution was rendered acidic (pH=3) to form precipitates, which were washed with water and dried at room temperature under reduced pressure to obtain 4.3 g of 7-[2-(5-methyl-6,7-dihydro-1-oxo-1H,5H-benzo[ij]quinolizine-2-carboxamido)-2-phenylacetamido]-3-(acetyloxymethyl)-8-oxo-5-thia-1-azabicyclo[4,2,0]oct-2-ene-2-carboxylic acid as white amorphous crystals having a melting point of 233°–237° C. (decomposition).

EXAMPLE 76

1.7 g of 8-(4-formyl-1-piperazinyl)-6,7-dihydro-1-oxo-1H,5H-benzo[ij]quinolizine-2-carboxylic acid was suspended in 25 ml of anhydrous dimethylformamide and 0.83 ml of triethylamine was added thereto and the mixture was stirred for 15 minutes while ice-cooling. Then, 0.8 ml of isobutyl chloroformate were added dropwise thereto while ice-cooling. After completion of addition, the mixture was stirred for 45 minutes while ice-cooling. On the other hand, 2.3 g of cephaloglycine was suspended to 30 ml of anhydrous dimethylformamide and 1.4 ml of triethylamine and 0.5 g of magnesium sulfate were added to the suspension. The resulting mixture was stirred at the same temperature as above for 30 minutes and insoluble materials were removed by filtration. The solution of triethylamine salt of cephaloglycine thus-obtained was added to the former reaction mixture and stirred for 2 hours while ice-cooling. After completion of the reaction, insoluble materials were removed by filtration and 5 ml of a 20% n-butanol solution of sodium 2-ethylhexanoate and then 250 ml of diethyl ether were added to the filtrate to precipitate crystals. The crystals were collected by filtration and dissolved in 150 ml of water and the solution was rendered acidic (pH=3) to form precipitates, which were washed with water and dried at room temperature under reduced pressure to obtain 2.1 g of 7-{2-[8-(4-formyl-1-piperazinyl)-6,7-dihydro-1-oxo-1H,5H-benzo[ij]quinolizine-2-carboxamido]-2-phenylacetamido}-3-(acetyloxymethyl)-8-oxo-5-thia-1-azabicyclo[4,2,0]oct-2-ene-2-carboxylic acid as light yellow amorphous crystals having a melting point of 261° to 265° C. (decomposition).

EXAMPLE 77

1.2 g of 5-methyl-1,3,4-thiadiazole-2-thiol was added to a mixture of 25 ml of acetonitrile and 3.4 g of cephalosporin derivative prepared in accordance with Example 75 followed by heat-refluxing for 5 hours while stirring. After completion of this reaction, the solvent was removed by evaporation under reduced pressure. The concentrate was washed with acetonitrile and then with acetone followed by drying in vacuum to obtain 2.5 g of 7-{2-[5-methyl-6,7-dihydro-1-oxo-1H,5H-benzo[ij]quinolizine-2-carboxamido]-2-phenylacetamido}-3-[2-(5-methyl-1,3,4-thiadiazole)thiomethyl]-8-oxo-5-thia-1-azabicyclo[4,2,0]oct-2-ene-2-carboxylic acid.

EXAMPLE 78

0.5 g of 1-methyl-1-H-tetrazole-5-thiol was added to a mixture of 15 ml of acetonitrile and 1.7 g of the cephalosporin derivative prepared in accordance with Example 75 followed by heat-refluxing for 6 hours while stirring. After completion of the reaction, the solvent was removed by evaporation under reduced pressure and the residue was dissolved in 10 ml of ethanol. A mixture of 5 ml of ethanol and 0.5 ml of dicyclohexylamine was added dropwise to the solution to obtain 7-[2-(5-methyl-6,7-dihydro-1-oxo-1H,5H-benzo[ij]quinolizine-2-carboxamido)-2-phenylacetamido]-3-[5-(1-methyl-1,2,3,4-tetrazole)thiomethyl]-8-oxo-5-thia-1-azabicyclo[4,2,-0]oct-2-ene-2-carboxylic acid dicyclohexylamine salt.

EXAMPLE 79

2.1 g of 6-oxo-1,2-dihydro-6H-pyrrolo[3,2,1-ij]quinoline-5-carboxylic acid was added to 50 ml of anhydrous dimethylformamide and 1.66 ml of triethylamine was added to the mixture while ice-cooling and stirred for 15 minutes. Then, 1.6 ml of isobutyl chloroformate was added thereto dropwise and stirred for 45 minutes while ice-cooling. On the other hand, 4.5 g of cephaloglycine was suspended in 60 ml of anhydrous dimethylformamide and 2.8 ml of triethylamine and 1 g of anhydrous sulfate were added to the resulting mixture while ice-cooling followed by stirring the mixture for 30 minutes. Insoluble materials were removed by filtration and the filtrate was added at one time to the former reaction mixture and allowed to react for 2 hours while ice-cooling. After completion of the reaction, insoluble materials were removed by filtration and the filtrate was mixed with 10 ml of a 20% butanol solution of sodium 2-ethylhexanoate followed by the addition of 500 ml of diethyl ether to precipitate crystals. The crystals were collected by filtration and dissolved in 300 ml of water. The resulting solution was rendered acidic (pH=3) with dilute hydrochloric acid to precipitate solid materials, which were washed with water and dried under reduced pressure to obtain 4.0 g of 7-[2-(1,2-dihydro-6-oxo-6H-pyrrolo[3,2,1-ij]quinoline-5-carboxamido)-2- phenylacetamido]-3-(acetyloxymethyl)-8-oxo-5-thia-1-azabicyclo[4,2,0]oct-2-ene-2-carboxylic acid as white amorphous crystals having a melting point of 245° to 248° C. (decomposition).

EXAMPLE 80

2.3 g of 2-methyl-1,2-dihydro-6-oxo-6H-pyrrolo[3,2,1-ij]quinoline-5-carboxylic acid was added to 50 ml of anhydrous dimethylformamide and 1.66 ml of triethylamine was added to the mixture while ice-cooling and stirred for 15 minutes. Then, 1.6 ml of isobutyl chloroformate was added thereto dropwise and stirred for 45 minutes while ice-cooling. On the other hand, 4.5 g of cephaloglycine was suspended in 60 ml of anhydrous dimethylformamide and 2.8 ml of triethylamine and 1 g of anhydrous magnesium sulfate were added to the resulting mixture while ice-cooling followed by stirring the mixture for 30 minutes. Insoluble materials were removed by filtration and the solution of the triethylamine salt of cephaloglycine thus-obtained was added at a time to the former reaction mixture and allowed to react for 2 hours while ice-cooling. After completion of the reaction, insoluble materials were removed by filtration and the filtrate was mixed with 10 ml of a 20% butanol solution of sodium 2-ethylhexanoate followed by the addition of 500 ml of diethyl ether to precipitate crystals. The crystals were collected by filtration and dissolved in 300 ml of water, and the resulting solution was rendered acidic (pH=3) with dilute hydrochloric acid to precipitate solid materials, which were washed with water and dried under reduced pressure to obtain 3.7 g of 7-[2-(2-methyl-1,2-dihydro-6-oxo-6H-pyrrolo[3,2,1-ij]quinoline-5-carboxamido)-2-phenylacetamido]-3-(acetyloxymethyl)-8-oxo-5-thia-1-azabicyclo[4,2,0]oct-2-ene-2-carboxylic acid.

EXAMPLE 81

1.34 g of 7a,8,9,10,11,11a-hexahydro-4-oxo-4H-pyrido[3,2,1-jk]carbazole-5-carboxylic acid was suspended to 50 ml of anhydrous dimethylformamide and 0.83 ml of triethylamine was added to the mixture and stirred for 15 minutes while ice-cooling. Then, 1.6 ml of isobutyl chloroformate was added thereto dropwise and stirred for 45 minutes while ice-cooling. On the other hand, 2.3 g of cephaloglycine was suspended in 30 ml of anhydrous dimethylformamide and 2.8 ml of triethylamine and 0.5 g of anhydrous magnesium sulfate were added to the resulting mixture while ice-cooling followed by stirring the mixture for 30 minutes. Insoluble materials were removed by filtration and the solution of the triethylamine salt of cephaloglycine thus-obtained was added at one time to the former reaction mixture and allowed to react for 2 hours while ice-cooling. After completion of the reaction, insoluble materials were removed by filtration and the filtrate was mixed with 5 ml of a 20% butanol solution of sodium 2-ethylhexanoate followed by the addition of 250 ml of diethyl ether to precipitate crystals. The crystals were collected by filtration and dissolved in 150 ml of water. The resulting solution was rendered acidic (pH=3) with dilute hydrochloric acid to precipitate solid materials, which were washed with water and dried under reduced pressure to obtain 2.2 g of 7-[2-(7a,8,9,10,11,11a-hexahydro-4-oxo-4H-pyrido-[3,2,1-jk]carbazole-5-carboxamido)-2-phenylacetamido]-3-(acetyloxymethyl)-8-oxo-5-thia-1-azabicyclo[4,2,0]oct-2-ene-2-carboxylic acid as white amorphous crystals having a melting point of 241 to 245° C. (decomposition).

PREPARATION EXAMPLE 1

| | |
|---|---|
| Sodium 6-[D-(—)-2-(7-a,8,9,10,11,11a-hexahydro-4-oxo-4H-pyrido[3,2,1-jk]-carbazole-5-carboxamido)-2-phenylacetamido]-3-,3-dimethyl-7-oxo-4-thia-1-azabicyclo[3,2,0]heptane-2-carboxylate | 200 mg |
| Glucose | 250 mg |
| Distilled Water for Injection | q.s. to make 5 ml |

The active compound and glucose were dissolved in distilled water for injection, and the solution was poured into a 5 ml ampoule. The air was purged with nitrogen, and the ampoule was sealed and sterilized at 121° C. for 15 minutes to obtain an injectable preparation.

PREPARATION EXAMPLE 2

| | |
|---|---|
| Sodium 6-[D-(—)-2-(6,7-dihydro-1-oxo-1H,5H-benzo[ij]quinolizine-2-carboxamido)-2-phenylacetamido]-3,3-dimethyl-7-oxo-4-thia-1-azabicyclo-[3,2,0]heptane-2-carboxylate | 200 mg |
| Glucose | 250 mg |
| Distilled Water for Injection | q.s. to make 5 ml |

The active compound and glucose were dissolved in distilled water for injection, and the solution was poured into a 5 ml ampoule. The air was purged with nitrogen, and the ampoule was sealed and sterilized at 121° C. for 15 minutes to obtain an injectable preparation.

PREPARATION EXAMPLE 3

| | |
|---|---|
| Sodium 6-[D-(—)-2-(1,2-dihydro-6-oxo-6H-pyrrolo[3,2,1-ij]quinoline-5-carboxamido)-2-phenylacetamido)-3,3-dimethyl-7-oxo-4-thia-1-azabicyclo-[3,2,0]heptane-2-carboxylate | 200 mg |
| Glucose | 250 mg |
| Distilled Water for Injection | q.s. to make 5 ml |

The active compound and glucose were dissolved in distilled water for injection, and the solution was poured into a 5 ml ampoule. The air was purged with nitrogen, and the ampoule was sealed and sterilized at 121° C. for 15 minutes to obtain an injectable preparation.

PREPARATION EXAMPLE 4

| | |
|---|---|
| 6-[D-(—)-2-(7a,8,9,10,11,11a-hexahydro-4-oxo-4H-pyrido[3,2,1-jk]carbazole-5-carboxamido)-2-phenylacetamido]-3,3-dimethyl-7-oxo-4-thia-1-azabicyclo-[3,2,0]heptane-2-carboxylic acid | 100 g |
| Avicel (trade name for a product of Asahi Kasei Kogyo Kabushiki Kaisha) | 40 g |
| Corn starch | 30 g |
| Magnesium Stearate | 2 g |
| TC-5 (trade name for hydroxypropyl-methyl cellulose, produced by Shinetsu Chemical Industry Co., Ltd.) | 10 g |
| Polyethylene Glycol-6000 (molecular weight: 6000) | 3 g |
| Castor Oil | 40 g |
| Methanol | 40 g |

The active compound, avicel, corn starch and magnesium stearate were mixed and ground, and then tableted using a conventional pounder (R 10 mm) for sugar coating (produced by Kikusui Seisakusho Co., Ltd.). The resulting tablets were coated with a film coating agent composed of TC-5, polyethylene glycol-6000, castor oil and methanol to produce film-coated tablets.

PREPARATION EXAMPLE 5

| | |
|---|---|
| 6-[D-(−)-2-(6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid | 2 g |
| Purified Hydrous Lanolin | 5 g |
| Japan Wax | 5 g |
| White Petrolatum | 88 g |
| Total: | 100 g |

Japan wax was heat-molten and the active compound, purified hydrous lanolin and white petrolatum were added thereto followed by heat-melting. The mixture was stirred until it began to solidify to prepare an ointment.

While the invention has been described in detail and with reference to specific embodiments thereof, it will be apparent to one skilled in the art that various changes and modifications can be made therein without departing from the spirit and scope thereof.

What is claimed is:

1. A β-lactam series compound represented by the formula (I):

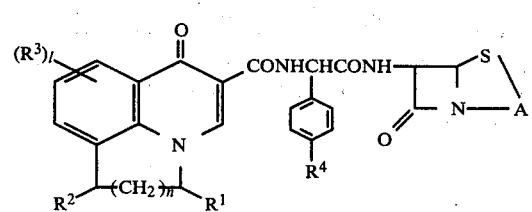

(I)

wherein $R^1$ represents a hydrogen atom or a lower alkyl group; $R^2$ represents a hydrogen atom; $R^3$ represents a halogen atom, a nitro group, an amino group, a hydroxy group, a lower alkyl group, a lower alkoxy group, a lower alkanoylamino group, a lower alkanesulfonyloxy group or a group represented by the formula

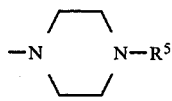

where $R^5$ represents a hydrogen atom, a lower alkanoyl group, or a lower alkanesulfonyl group; $R^4$ represents a hydrogen atom or a hydroxy group; n is an integer of 0 or 1; l is 0, 1 or 2; and A represents —C(CH$_3$)$_2$CH(COOH)— or —CH$_2$C(CH$_2$R$^6$)=C(COOH)— where $R^6$ represents a lower alkanoyloxy group, a group represented by the formula

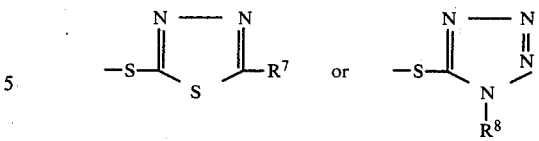

where $R^7$ and $R^8$ each represents a lower alkyl group, and when n is 0, $R^1$ and $R^2$ can combine to form a cyclohexane ring together with the carbon atoms to which they are attached, and pharmaceutically acceptable salts.

2. The compound of claim 1, wherein $R^1$ and $R^2$ do not combine to form a cyclohexane ring.

3. The compound of claim 2, wherein $R^3$ is a group represented by the formula

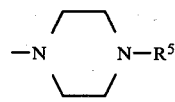

where $R^5$ represents a hydrogen atom, a lower alkanoyl group, or a lower alkanesulfonyl group and l is 1 or 2.

4. The compound of claim 2, wherein $R^3$ represents a halogen atom and l is 1 or 2.

5. The compound of claim 2, wherein $R^3$ represents a nitro group and l is 1 or 2.

6. The compound of claim 2, wherein $R^3$ represents a lower alkoxy group and l is 1 or 2.

7. The compound of claim 2, wherein $R^3$ represents a lower alkyl group and l is 1 or 2.

8. The compound of claim 2, wherein $R^3$ represents a hydroxy group and l is 1 or 2.

9. The compound of claim 2, wherein $R^3$ represents an amino group and l is 1 or 2.

10. The compound of claim 2, wherein $R^3$ represents a lower alkanoylamino group and l is 1 or 2.

11. The compound of claim 2, wherein $R^3$ represents a lower alkanesulfonyloxy group.

12. The compound of claim 2, wherein l is 0.

13. The compound of claim 1, wherein n is 0, and $R^1$ and $R^2$ combine to form a cyclohexane ring together with the carbon atoms to which they are attached.

14. The compound of claim 13, wherein l is 0.

15. The compound of claim 13, wherein $R^3$ represents a halogen atom and l is 1 or 2.

16. The compound of claim 13, wherein $R^3$ represents a nitro group, an amino group, a hydroxy group, a lower alkyl group, a lower alkoxy group, a lower alkanoylamino group, a lower alkanesulfonyloxy group or a group represented by the formula

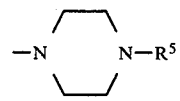

wherein $R^5$ represents a hydrogen atom, a lower alkanoyl group, or a lower alkanesulfonyl group and l is 1 or 2.

17. 6-[2-(6,7-Dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid.

18. 6-[2-(5-Methyl-6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid.

19. 6-[2-(5-Methyl-6,7-dihydro-1-oxo-1H,5H-benzo[ij]quinolizine-2-carboxamido)-2-(4-hydroxy)-phenylacetamido]-3,3-dimethyl-7-oxo-4-thia-1-azabicyclo[3,2,0]heptane-2-carboxylic acid 20. 6-{2-[8-(1-Piperazinyl)-6,7-dihydro-1-oxo-1H,5H-benzo[ij]quinolizine-2-carboxamido]-2-phenylacetamido}-3,3-dimethyl-7-oxo-4-thia-1-azabicyclo[3,2,0]heptane-2-carboxylic acid.

21. 6-{2-[8-(4-Acetyl-1-piperazinyl)-6,7-dihydro-1-oxo-1H,5H-benzo[ij]quinolizine-2-carboxamido]-2-phenylacetamido}-3,3-dimethyl-7-oxo-4-thia-1-azabicyclo[3,2,0]heptane-2-carboxylic acid.

22. 6-[2-(9-Fluoro-6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid.

23. 6-[2-(9-Methyl-6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid.

24. 6-[2-(9-Hydroxy-6,7-dihydro-1-oxo-1H,5H-benzo[ij]quinolizine-2-carboxamido)-2-phenylacetamido]-3,3-dimethyl-7-oxo-4-thia-1-azabicyclo[3,2,0]heptane-2-carboxylic acid.

25. 6-[2-(6,7-Dihydro-1-oxo-1H,5H-benzo[ij]quinolizine-2-carboxamido)-2-(4-hydroxy)phenylacetamido]-3,3-dimethyl-7-oxo-4-thia-1-azabicyclo[3,2,0]heptane-2-carboxylic acid.

26. 7-[2-(6,7-Dihydro-1-oxo-1H,5H-benzo[ij]quinolizine-2-carboxamido)-2-phenylacetamido]-3-(acetyloxymethyl)-8-oxo-5-thia-1-azabicyclo[4,2,0]oct-2-ene-2-carboxylic acid.

27. 6-[2-(1,2-Dihydro-6-oxo-6H-pyrrolo[3,2,1-ij]quinoline-5-carboxamido)-2-phenylacetamido]-3,3-dimethyl-7-oxo-4-thia-1-azabicyclo[3,2,0]heptane-2-carboxylic acid.

28. 6-[D-(−)-2-(8-Fluoro-1,2-dihydro-6-oxo-6H-pyrrolo[3,2,1-ij]quinoline-5-carboxamido)-2-(4-hydroxy)-phenylacetamido]-3,3-dimethyl-7-oxo-4-thia-1-azabicyclo[3,2,0]heptane-2-carboxylic acid.

29. 6-[2-(7a,8,9,10,11,11a-hexahydro-4-oxo-4H-pyrido[3,2,1-jk]carbazole-5-carboxamido)-2-phenylacetamido]-3,3-dimethyl-7-oxo-4-thia-1-azabicyclo[3,2,0]heptane-2-carboxylic acid.

30. 6-[2-(2-Fluoro-7a,8,9,10,11,11a-hexahydro-4-oxo-4H-pyrido[3,2,1-jk]carbazole-5-carboxamido)-2-phenylacetamido]-3,3-dimethyl-7-oxo-4-thia-1-azabicyclo[3,2,0]heptane-2-carboxylic acid.

31. 6-[2-(7a,8,9,10,11,11a-Hexahydro-4-oxo-4H-pyrido[3,2,1-jk]carbazole-5-carboxamido)-2-(4-hydroxy)phenylacetamido]-3,3-dimethyl-7-oxo-4-thia-1-azabicyclo[3,2,0]heptane-2-carboxylic acid.

32. A pharmaceutical preparation having anti-bacterial effects, containing a pharmaceutically acceptable carrier and a therapeutically effective amount of a compound of the formula (I):

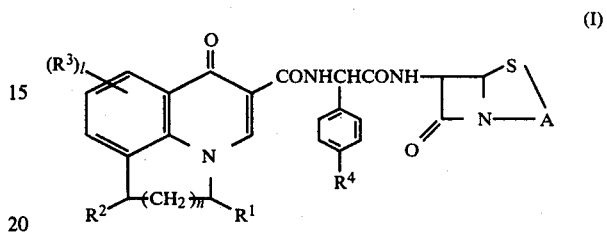

wherein $R^1$ represents a hydrogen atom or a lower alkyl group; $R^2$ represents a hydrogen atom; $R^3$ represents a halogen atom, a nitro group, an amino group, a hydroxy group, a lower alkyl group, a lower alkoxy group, a lower alkanoylamino group, a lower alkanesulfonyloxy group or a group represented by the formula

wherein $R^5$ represents a hydrogen atom, a lower alkanoyl group, or a lower alkanesulfonyl group; $R^4$ represents a hydrogen atom or a hydroxy group; n is an integer of 0 or 1; l is 0, 1 or 2; and A represents —C(CH$_3$)$_2$CH(COOH)— or —CH$_2$C(CH$_2$R$^6$)=C(COOH)— where $R^6$ represents a lower alkanoyloxy group, a group represented by the formula

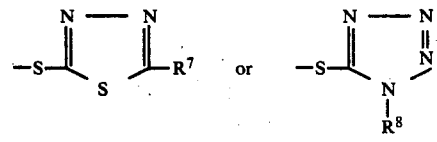

where $R^7$ and $R^8$ each represents a lower alkyl group, and when n is 0, $R^1$ and $R^2$ can combine to form a cyclohexane ring together with the carbon atoms to which they are attached, and pharmaceutically acceptable salts.

* * * * *